(12) United States Patent
Tachikawa et al.

(10) Patent No.: US 10,683,500 B2
(45) Date of Patent: *Jun. 16, 2020

(54) UNA OLIGOMERS HAVING REDUCED OFF-TARGET EFFECTS IN GENE SILENCING

(71) Applicant: Arcturus Therapeutics, Inc., San Diego, CA (US)

(72) Inventors: Kiyoshi Tachikawa, San Diego, CA (US); Joseph E. Payne, San Diego, CA (US); Padmanabh Chivukula, San Diego, CA (US)

(73) Assignee: Arcturus Therapeutics, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/109,231

(22) Filed: Aug. 22, 2018

(65) Prior Publication Data

US 2018/0362985 A1  Dec. 20, 2018

Related U.S. Application Data

(63) Continuation of application No. 14/667,680, filed on Mar. 25, 2015.

(60) Provisional application No. 61/970,320, filed on Mar. 25, 2014.

(51) Int. Cl.
| | | |
|---|---|---|
| C12N 15/113 | (2010.01) | |
| A61K 31/713 | (2006.01) | |
| A61K 47/14 | (2017.01) | |

(52) U.S. Cl.
CPC .......... *C12N 15/113* (2013.01); *A61K 31/713* (2013.01); *A61K 47/14* (2013.01); *C12N 2310/14* (2013.01); *C12N 2310/323* (2013.01)

(58) Field of Classification Search
None
See application file for complete search history.

(56) References Cited

U.S. PATENT DOCUMENTS

| | | | |
|---|---|---|---|
| 4,199,574 A | 4/1980 | Schaeffer | |
| 4,968,686 A | 11/1990 | Townsend | |
| 5,786,359 A | 7/1998 | Reitz | |
| 5,898,031 A | 4/1999 | Crooke | |
| 6,037,176 A | 3/2000 | Bennett | |
| 6,069,132 A | 5/2000 | Revanker | |
| 6,506,559 B1 | 1/2003 | Fire et al. | |
| 6,608,035 B1 | 8/2003 | Agrawal | |
| 6,753,139 B1 | 6/2004 | Baulcombe | |
| 7,056,704 B2 | 6/2006 | Tuschl | |
| 7,078,196 B2 | 7/2006 | Tuschl | |
| 7,459,547 B2 | 12/2008 | Zamore et al. | |
| 7,579,451 B2 | 8/2009 | Manoharan | |
| 7,691,995 B2 | 4/2010 | Zamore | |
| 7,745,608 B2 | 6/2010 | Manoharan | |
| 7,750,144 B2 | 7/2010 | Zamore | |
| 7,786,290 B2 | 8/2010 | Woppmann | |
| 7,915,399 B2 | 3/2011 | MacLachlan | |
| 8,101,584 B2 | 1/2012 | Kreutzer | |
| 8,101,742 B2 | 1/2012 | Kreutzer | |
| 8,258,285 B2 | 9/2012 | Baulcombe | |
| 8,314,227 B2 | 11/2012 | Wengel | |
| 8,362,231 B2 | 1/2013 | Tuschl | |
| 8,420,391 B2 | 4/2013 | Tuschl | |
| 8,546,143 B2 | 10/2013 | Kreutzer | |
| 9,051,570 B2 | 6/2015 | Wengel | |
| 9,365,610 B2 | 6/2016 | Payne | |
| 9,856,475 B2 | 1/2018 | Tachikawa et al. | |
| 9,982,259 B2 | 5/2018 | Tachikawa et al. | |
| 10,421,964 B2 * | 9/2019 | Tachikawa | A61K 31/713 |
| 2002/0086356 A1 | 7/2002 | Tuschl | |
| 2003/0143732 A1 | 7/2003 | Fosnaugh | |
| 2004/0171570 A1 | 9/2004 | Allerson | |
| 2004/0175703 A1 | 9/2004 | Kreutzer et al. | |
| 2004/0192626 A1 | 9/2004 | McSwiggen et al. | |
| 2004/0259247 A1 | 12/2004 | Tuschl et al. | |
| 2004/0261149 A1 | 12/2004 | Fauquet et al. | |
| 2005/0100907 A1 | 5/2005 | Kreutzer | |
| 2005/0107325 A1 | 5/2005 | Manoharan | |
| 2005/0129778 A1 | 6/2005 | Mulye | |
| 2005/0223427 A1 | 10/2005 | Khvorova | |
| 2005/0244858 A1 | 11/2005 | Rossi et al. | |
| 2005/0288244 A1 | 12/2005 | Manoharan | |
| 2006/0122391 A1 | 6/2006 | Babu | |
| 2006/0276635 A1 | 12/2006 | McSwiggen | |
| 2006/0287260 A1 | 12/2006 | Manoharan | |
| 2007/0275914 A1 | 11/2007 | Manoharan | |
| 2009/0093438 A1 | 4/2009 | McSwiggen | |

(Continued)

FOREIGN PATENT DOCUMENTS

| | | |
|---|---|---|
| WO | WO-9629336 A1 | 9/1996 |
| WO | WO-9908688 A1 | 2/1999 |

(Continued)

OTHER PUBLICATIONS

Bartlett, "Effect of siRNA Nuclease Stability on the In Vitro and In Vivo Kinetics of siRNA-Mediated Gene Silencing," Biotechnology and Bioengineering, vol. 97, No. 4, Jul. 1, 2007.

(Continued)

*Primary Examiner* — J. E Angell
(74) *Attorney, Agent, or Firm* — Mintz Levin; Marc Morley; Mridula Sherin

(57) ABSTRACT

This invention provides UNA oligomers for gene silencing with reduced off-target effects. The UNA oligomers can have a first strand and a second strand, each of the strands being 19-29 monomers in length, the monomers being UNA monomers and various nucleic acid monomers. Embodiments include pharmaceutical compositions and methods for treating or preventing TTR-related amyloidosis with reduced off-target effects by administering a UNA oligomer to a subject.

10 Claims, 13 Drawing Sheets

Specification includes a Sequence Listing.

(56) References Cited

U.S. PATENT DOCUMENTS

| | | |
|---|---|---|
| 2010/0120893 A1 | 5/2010 | Baligh et al. |
| 2011/0136233 A1 | 6/2011 | Quay et al. |
| 2011/0313020 A1 | 12/2011 | Templin et al. |
| 2012/0120893 A1 | 5/2012 | Baligh et al. |
| 2012/0225927 A1 | 9/2012 | Sah |
| 2013/0096289 A1 | 4/2013 | Wengel |
| 2013/0190383 A1 | 7/2013 | Vaish et al. |
| 2013/0281510 A1 | 10/2013 | Ando et al. |
| 2014/0275211 A1 | 9/2014 | Sah et al. |
| 2014/0315835 A1 | 10/2014 | Rajeev |
| 2015/0141678 A1 | 5/2015 | Payne et al. |
| 2015/0307880 A1 | 10/2015 | Tachikawa |
| 2015/0307881 A1 | 10/2015 | Tachikawa et al. |
| 2015/0368644 A1 | 12/2015 | Collard et al. |

FOREIGN PATENT DOCUMENTS

| | | |
|---|---|---|
| WO | WO-2003004602 A2 | 1/2003 |
| WO | WO-2003037909 A1 | 5/2003 |
| WO | WO-03070918 A2 | 8/2003 |
| WO | WO-03106477 A1 | 12/2003 |
| WO | WO-2004090105 A2 | 10/2004 |
| WO | WO-2004090108 A2 | 10/2004 |
| WO | WO-2004094595 A2 | 11/2004 |
| WO | WO-2004108897 A2 | 12/2004 |
| WO | WO-2005089268 A2 | 9/2005 |
| WO | WO-2005089287 A2 | 9/2005 |
| WO | WO-2005121372 A2 | 12/2005 |
| WO | WO-06085987 A2 | 8/2006 |
| WO | WO-2006112872 A2 | 10/2006 |
| WO | WO-2007022369 A2 | 2/2007 |
| WO | WO-2007051303 A1 | 5/2007 |
| WO | WO-2007056829 A1 | 5/2007 |
| WO | WO-2008020435 A2 | 2/2008 |
| WO | WO-08147824 A2 | 12/2008 |
| WO | WO-2008147824 | 12/2008 |
| WO | WO-2010017319 | 2/2010 |
| WO | WO-2010048228 | 4/2010 |
| WO | WO-2010065756 | 6/2010 |
| WO | WO-2011123468 A1 | 10/2011 |
| WO | WO-2011133584 A2 | 10/2011 |
| WO | WO-2011139710 | 11/2011 |
| WO | WO-2012058268 | 5/2012 |
| WO | WO-2012177906 | 12/2012 |
| WO | WO-2013075035 | 5/2013 |
| WO | WO-2014037436 A1 | 3/2014 |
| WO | WO-2015042564 A1 | 3/2015 |
| WO | WO-2015148580 | 10/2015 |
| WO | WO-2015148582 | 10/2015 |

OTHER PUBLICATIONS

Bramsen et al., "A large-scale chemical modification screen identifies design rules to generate siRNAs with high activity, high stability and low toxicity," Nucleic Acids Research 2009, vol. 37, No. 9, pp. 2867-2881.

Bramsen, Jesper B., et al., "A screen of chemical modifications identifies position-specific modification by UNA to most potently reduce siRNA off-target effects." Nucleic acids research 38.17 (2010): 5761-5773.

Czauderna, Frank, et al., "Structural variations and stabilising modifications of synthetic siRNAs in mammalian cells." Nucleic acids research 31.11 (2003): 2705-2716.

Elbashir, Sayda M., et al. "Functional anatomy of siRNAs for mediating efficient RNAi in *Drosophila melanogaster* embryo lysate." The EMBO journal 20.23 (2001): 6877-6888.

Habus, "Oligonucleotides Containing Acyclic Nucleoside Analogues with Carbamate Internucleoside Linkages," Nucleosides & Nucleotides, 1995, vol. 14 (9&10), 1853-1859.

Jensen, T. et al., "Unlocked Nucleic Acid (UNA) and UNA Derivatives: Thermal Denaturation Studies," Nucleic Acids Symposium Series No. 52; Oxford University Press 2008; pp. 133-134.

John Wiley & Sons, Inc.; "IUPAC-IUB Joint Commission on Biochemical Nomenclature Abbreviations and Symbols for the Description of Conformations of Polynucleotide Chains," Current Protocols in Nucleic Acid Chemistry 2000; pp. A.1C.1-A.1D.3.

Langkjær, Niels, et al., "UNA (unlocked nucleic acid): a flexible RNA mimic that allows engineering of nucleic acid duplex stability." Bioorganic & medicinal chemistry 17.15 (2009): 5420-5425.

Laursen, Maria B., et al., "Utilization of unlocked nucleic acid (UNA) to enhance siRNA performance in vitro and in vivo." Molecular BioSystems 6.5 (2010): 862-870.

Layzer, "In vivo activity of nuclease-resistant siRNAs," RNA (2004), vol. 10, pp. 766-771.

Mangos, M. et al., "Efficient RNase H-Directed Cleavage of RNA Promoted by Antisense DNA or 2'F-ANA Constructs Containing Acyclic Nucleotide Inserts," Journal of the American Chemical Society 2003; vol. 125; pp. 654-661.

Nielsen, "Oligonucleotide Analogues Containing 4'-C-(Hydroxymethyl)uridine: Synthesis, Evaluation and Mass Spectrometric Analysis," Bioorganic & Medicinal Chemistry, vol. 3, No. 11, pp. 1493-1502, 1995.

Nielsen, P. et al.; "Synthesis and Evaluation of Oligodeoxynucleotides Containing Acyclic Nucleosides: Introduction of Three Novel Analogues and a Summary," Bioorganic & Medicinal Chemistry; Elsevier Science Ltd 1995; vol. 3; No. 1; pp. 19-28.

Pandolfi, "Evaluation of Different Types of End-Capping Modifications on the Stability of Oligonucleotides Toward 3'- and 5' Exonucleases," Nucleosides & Nucleotides, 1999, vol. 18 (9), 2051-2069.

Pei et al., "Synthesis of 3'-C-Hydroxymethyl-substituted Pyrimidine and Purine Nucleosides as Potential Anti-Hepatitis C Virus (HCV) Agents," Arch Pharm Res 2009, vol. 31, No. 7, pp. 843-849.

Petersen, "LNA: A versatile tool for therapeutics and genomics," Trends in Biotechnology vol. 21 No. 2 Feb. 2003.

Pfundheller, "Locked Nucleic Acid Synthesis," Chapter 8 in Methods in Molecular Biology, vol. 288: Oligonucleotide Synthesis: Methods and Applications, Edited by: P. Herdewijn, Humana Press, 2005.

pharmabiz.com, Arcturus to present gene knockdown data in non-human primates, showing up to 94% reduction in gene expression with single low dose, dated Oct. 14, 2014.

Snead, Nicholas M., et al., "5' Unlocked nucleic acid modification improves siRNA targeting." Molecular Therapy-Nucleic Acids 2 (2013): 7 Pages.

Thrane, H. et al.; "Novel Linear and Branched Oligodeoxynucleotide Analogues Containing 4'-C-(Hydroxymethyl Thymidine;" Tetrahedron; Elsevier Science Ltd 1995; vol. 51; No. 37; pp. 10389-10402.

Vaish, Narendra, et al., "Improved specificity of gene silencing by siRNAs containing unlocked nucleobase analogs." Nucleic acids research 39.5 (2010): 1823-1832.

Werk, Denise, et al., "Application of small interfering RNAs modified by unlocked nucleic acid (UNA) to inhibit the heart-pathogenic coxsackievirus B3." FEBS letters 584.3 (2010): 591-598.

* cited by examiner

| Duplex ID | Position | Oligo Sense Seq (21mer)[5'-->3'] | Oligo Antisense Seq (21mer)[5'-->3'] |
|---|---|---|---|
| ATS-24 | 628 | GuAAccAAGAGuAuuccAudTdT | AUGGAAuACUCUUGGUuACdTdT |
| ATS-91 | | GUAACCAAGAGUAUUCCAUdTdT | AUGGAAUACUCUUGGUUACdTdT |
| ATX-14 | | GUAACCAAGAGUAUUCCAUdTdT | AUGGAAUACUCUUGGUUACdTdT |
| ATX-16 | | GUAACCAAGAGUAUUCCAUÜÜ | AUGGAAUACUCUUGGUUACÜÜ |
| ATX-13 | | GUAACCAAGAGUAUUCCAUdTdT | AUGGAAUACUCUUGGUUACdTdT |
| ATX-15 | | GUAACCAAGAGUAUUCCAUÜÜ | AUGGAAUACUCUUGGUUACÜÜ |
| ATX-17 | | GUAACCAAGAGUAUUCCAUÜÜ | AUGGAAUACUCUUGGUUACÜÜ |
| ATX-21 | | GUAACCAAGAGUAUUCCAÜmU | AUGGAAUACUCUUGGUUACÜmU |
| ATS-92 | 626 | AUGUAACCAAGAGUAUUCCdTdT | GGAAUACUCUUGGUUACAUdTdT |
| ATX-25 | | AUGUAACCAAGAGUAUUCC0mU | GGAAUACUCUUGGUUACAU0mU |

SEQ ID NOs: 45-54  SEQ ID NOs: 55-64

FIG. 4

SEQ ID NOs: 69-79

| Target sequence | 5'- CAUGUAACCAAGAGUAUUCCAUUUUA-3' |
|---|---|
| ATS- 92 (626) | AUGUAACCAAGAGUAUUCCdTdT |
| ATX- 25 (626) | AUGUAACCAAGAGUAUUCCUmU |
| ATS-104 (627) | UGUAACCAAGAGUAUUCCAdTdT |
| ATX- 37 (627) | UGUAACCAAGAGUAUUCCAUmU |
| ATS- 91 (628) | GUAACCAAGAGUAUUCCAUdTdT |
| ATX- 21 (628) | GUAACCAAGAGUAUUCCAUUmU |
| ATS-105 (629) | UAACCAAGAGUAUUCCAUUdTdT |
| ATX- 38 (629) | UAACCAAGAGUAUUCCAUUUmU |
| ATS-106 (632) | CCAAGAGUAUUCCAUUUUUdTdT |
| ATX- 39 (632) | CCAAGAGUAUUCCAUUUUUUmU |

FIG. 6

ATS

SEQ ID NO: 80
5'— N·N·N·N·N·N·N·N·N·N·N·N·N·N·N·N·N·N·N·NdTdT —3'

SEQ ID NO: 81
3'—dTdTN·N·N·N·N·N·N·N·N·N·N·N·N·N·N·N·N·N·N·N —5'

ATX

SEQ ID NO: 82
1—X·N·N·N·N·N·N·N·N·N·N·N·N·N·N·N·N·N·N·N·XmU —3'

SEQ ID NO: 83
3'—mUX·N·N·N·N·N·N·N·N·N·N·N·N·N·N·N·N·N·N·N·N —5'

UNA Oligomer

FIG. 7

UNA OLIGOMERS HAVING REDUCED OFF-TARGET EFFECTS IN GENE SILENCING

SEQUENCE LISTING

This application includes a Sequence Listing submitted electronically herewith as an ASCII file created on Aug. 22, 2018, named ARC1246WO_SL.txt, which is 31,009 bytes in size, and is hereby incorporated by reference in its entirety.

BACKGROUND OF THE INVENTION

A major drawback of gene silencing techniques such as RNA interference is the occurrence of off-target effects. Off-target effects occur when a gene-silencing agent has an effect on a gene product to which it is not targeted, and is therefore unwanted. Off-target effects loom as one of the main hurdles for developing gene silencing therapeutics.

One method to reduce off-target effects is to intelligently design the structure of the gene silencing agent to avoid effects on genes other than the desired target. In some cases, the gene silencing agents could be pooled so that the concentration of agents having a particular off-target effect would be reduced. In other cases, the gene silencing agent could be chemically modified to avoid off-targets effects. These conventional methods have been able to reduce off-target effects, however, they can be difficult to carry out.

What is needed are gene silencing agents with reduced off target effects.

There is a long-standing need for methods and compositions for therapeutic oligomers that operate via RNA interference, which avoid or reduce off target effects.

BRIEF SUMMARY

This invention provides active agents for gene silencing and methods for using the active agents in treating or preventing disease.

In particular, the active agents are UNA oligomers having reduced off-target effects in gene silencing.

The UNA oligomers of this invention are unlocked nucleomonomer active agents (UNA), described in detail below.

The UNA oligomers of this invention can be effective for gene silencing with reduced off-target effects for a wide range of gene targets.

In certain aspects, this invention provides UNA oligomers for inhibiting ApoCIII expression.

In some aspects, this invention provides therapeutics for amyloidosis. More particularly, this invention relates to methods for treating transthyretin-related amyloidosis with UNA oligomers having reduced off-target effects in knockdown of transthyretin.

In certain aspects, this invention provides UNA oligomers for inhibiting TTR expression, and V30M TTR expression, which can be used in treating amyloidosis with reduced off-target effects. The UNA oligomers can have a first strand and a second strand, each of the strands being 19-29 monomers in length, the monomers being UNA monomers and nucleic acid monomers. Embodiments include pharmaceutical compositions and methods for treating or preventing TTR-related amyloidosis with reduced off-target effects by administering a UNA oligomer to a subject.

In certain aspects, UNA oligomers of this invention can be used for gene silencing in plants.

Embodiments of this invention include the following:

A UNA oligomer for inhibiting expression of a target gene, the oligomer comprising a first strand and a second strand, each of the strands being 19-29 monomers in length, the monomers comprising UNA monomers and nucleic acid monomers, wherein the oligomer has a duplex structure of from 14 to 29 monomers in length, and wherein the oligomer has reduced off-target effects as compared to a siRNA with the same target.

The UNA oligomer above, wherein the second strand is a guide strand for RNA interference, and the first strand is a passenger strand for RNA interference. The UNA oligomer above, wherein the UNA oligomer has a UNA monomer at the first position at the 1 end of the first strand, a UNA monomer at one or both of the last two positions from the 3 end of the first strand, and a UNA monomer at one or both of the last two positions from the 3 end of the second strand.

The UNA oligomer above, wherein the UNA oligomer has a UNA monomer at the first position at the 1 end of the first strand, and a UNA monomer at one or both of the last two positions from the 3 end of the first strand. The UNA oligomer above, wherein the UNA oligomer has a UNA monomer at the first position at the 1 end of the first strand, and a UNA monomer at one or more of the last two positions from the 3 end of the second strand.

The UNA oligomer above, wherein the UNA oligomer has a UNA monomer at the first position at the 1 end of the first strand. The UNA oligomer above, wherein the UNA oligomer has a UNA monomer at one or more of the last two positions from the 3 end of the first strand, and a UNA monomer at one or more of the last two positions from the 3 end of the second strand.

The UNA oligomer above, wherein the UNA oligomer has one or two overhangs. The UNA oligomer above, wherein the UNA oligomer inhibits TTR expression with reduced off-target effects. The UNA oligomer above, wherein the UNA oligomer inhibits apolipoprotein gene expression with reduced off-target effects.

The UNA oligomer above, wherein the oligomer inhibits TTR expression in vivo.

The UNA oligomer above, wherein the UNA oligomer is targeted to inhibit gene expression in a plant with reduced off-target effects.

The UNA oligomer above, comprising at least one nucleic acid monomer that is base-modified, sugar-modified, or linkage modified.

The UNA oligomer above, wherein the oligomer comprises a sequence selected from the group of SEQ ID NOs:3-32.

The UNA oligomer above, wherein the oligomer comprises a UNA monomer at any one or more of positions 2-8 from the 5' end of the second strand.

A pharmaceutical composition comprising a UNA oligomer above and a pharmaceutically acceptable carrier.

The pharmaceutical composition above, wherein the composition is capable of local or systemic administration.

The pharmaceutical composition above, wherein the composition is capable of intravenous, subcutaneous, pulmonary, intramuscular, intraperitoneal, dermal, or oral administration.

The pharmaceutical composition above, comprising a lipid formulation.

The pharmaceutical composition above, comprising one or more lipids selected from cationic lipids, anionic lipids, sterols, pegylated lipids, and any combination of the foregoing.

The pharmaceutical composition above, wherein the composition is substantially free of liposomes.

The pharmaceutical composition above, wherein the composition contains liposomes.

A method for treating or preventing TTR-related amyloidosis, comprising administering to a subject in need an effective amount of a UNA oligomer above.

The method above, wherein the TTR-related amyloidosis is ATTR. The method above, wherein the subject is human. The method above, wherein the method reduces TTR in the subject with off-target effects reduced by at least 10% as compared to control.

The method above, wherein the effective amount is a dose of from 0.001 to 50.0 mg/kg. The method above, wherein TTR mRNA expression is reduced for at least 5 days.

The method above, wherein the method reduces peripheral neuropathy or autonomic neuropathy in the subject.

A method for inhibiting expression of a TTR gene in a cell, comprising treating the cell with a UNA oligomer above.

A method for inhibiting expression of a TTR gene in a mammal, comprising administering to the mammal a UNA oligomer above.

A method for inhibiting expression of a gene in a plant, comprising administering to the plant a UNA oligomer having a length of from 10 to 1000 base pairs.

BRIEF DESCRIPTION OF THE DRAWINGS

FIG. 4 shows the structures of UNA oligomers ATX13, ATX15 and ATX21.

FIG. 6 shows the structures of UNA oligomers that were used in a head-to-head comparison against conventional siRNAs for knockdown levels. The UNA oligomers were tiled around position 284 in the TTR mRNA region from position 625 to position 651. Five UNA oligomers were prepared, namely ATX25, ATX37, ATX21, ATX38 and ATX39. These UNA oligomers were tested for off-target effects as compared to conventional siRNAs targeted to the same positions.

FIG. 7 shows the structure of embodiments of UNA oligomers that have reduced off-target effects.

DETAILED DESCRIPTION OF THE INVENTION

Figure 1:
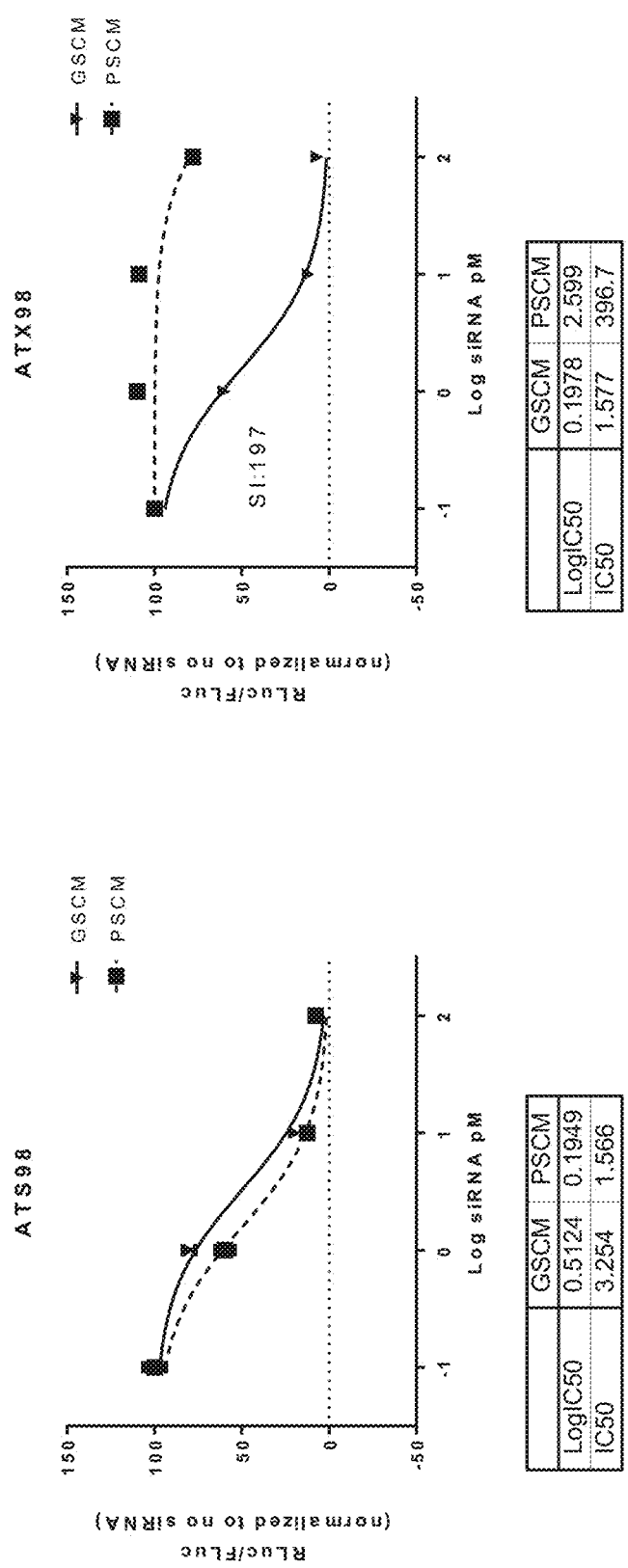
FIG. 1 shows that a UNA oligomer demonstrated surprisingly reduced off target activity for ApoCIII mRNA expression in a dual Luciferase reporter assay using PSICHECK-2 VECTOR (Promega). In particular, UNA oligomer ATX98 having UNA monomers in the passenger strand located at the 5' end position 1 (Ã) and at position 20 (Ũ), as well as in the guide strand at position 20 (Ũ) had greatly reduced off target knockdown activity by the passenger strand (PSCM) as compared to a comparable UNA oligomer ATS98, which did not have a UNA monomer in the passenger strand located at the 5' end position 1 (Ã). The UNA oligomer ATX98 had over 250-fold reduced off target knockdown.

This invention relates to the fields of biopharmaceuticals and therapeutics that are operable by gene silencing. More particularly, this invention relates to the structures, compositions and uses of active agents that have reduced off-target effects in gene silencing. The active agents are UNA oligomers that can be used for gene silencing, and among other things, in methods for treating transthyretin-related amyloidosis.

This invention provides UNA oligomers that are active agents for gene silencing, and methods for using the UNA oligomers in treating or preventing disease. The UNA oligomers of this invention can have reduced off-target effects in gene silencing.

The UNA oligomers of this invention are unlocked nucleomonomer active agents (UNA), which are described in detail below. A UNA oligomer is a chain molecule that includes one or more UNA monomers. A UNA monomer is a small organic molecule based on a propane-1,2,3-tri-yl-trisoxy structure. A UNA oligomer can be a chain composed of UNA monomers, as well as various nucleotides that may be based on naturally-occurring nucleosides or modified nucleotides.

In some aspects, this invention provides therapeutics for amyloidosis. More particularly, this invention relates to methods for treating transthyretin-related amyloidosis with UNA oligomers having reduced off-target effects in knockdown of transthyretin.

In certain aspects, UNA oligomers of this invention can be used for gene silencing in plants. UNA oligomers for use in plants may have lengths from 10 to 1000 base pairs. UNA oligomers of this invention can be used for functional genomics in plants, for controlling plant traits, for providing resistance to viruses and pathogens, or for providing protection from insects, among other things, while providing reduced off target effects.

The UNA oligomers of this invention can be active for specific gene knockdown with reduced off-target effects.

In some embodiments, a UNA oligomer is targeted to a gene target that is validated as being a disease target.

In certain embodiments, a UNA oligomer of this disclosure can be targeted to a transthyretin (TTR) gene.

In further embodiments, a UNA oligomer of this disclosure can be targeted to an apolipoprotein gene, such as ApoCIII.

Amyloidosis related to transthyretin (ATTR) involves the depositing of amyloid fibril proteins in various organs and tissues, including the peripheral, autonomic, and central nervous systems. Transthyretin (TTR) is a secreted thyroid hormone-binding protein that binds and transports retinol binding protein, and serum thyroxine in plasma and cerebrospinal fluid.

Symptoms of ATTR often include neuropathy and/or cardiomyopathy. Peripheral neuropathy can begin in the lower extremities, with sensory and motor neuropathy, and can progress to the upper extremities. Autonomic neuropathy can be manifest by gastrointestinal symptoms and orthostatic hypotension.

The most common mutation of the TTR gene in patients with ATTR is Val-30-Met. The major treatment for ATTR amyloidosis is liver transplantation, which removes the major source of variant TTR production and replaces it with normal TTR. There is currently no pharmacological therapy that can undo the formation of TTR amyloid.

In some embodiments, this invention provides active agents for efficient gene silencing and knockdown of TTR with reduced off target effects.

In some embodiments, UNA oligomers are provided for treating amyloidosis related to transthyretin (ATTR). The UNA oligomers of this invention can reduce the depositing of amyloid fibril proteins in various organs and tissues, including the peripheral, autonomic, and central nervous systems.

In certain aspects, this invention provides therapeutics for ATTR and related amyloid-related diseases.

Aspects of this invention include UNA oligomers that can be used for treating clinical features of ATTR amyloidosis, including neuropathy and/or cardiomyopathy.

In some embodiments, UNA oligomers of this invention are targeted to one mutation Val-30-Met TTR.

This invention can provide a pharmacological therapy that can undo the formation of TTR amyloid.

UNA Monomers

UNA monomers are small organic molecules based on a propane-1,2,3-tri-yl-trisoxy structure as shown below:

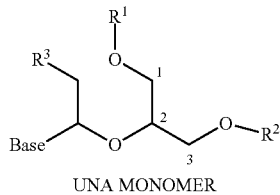

UNA MONOMER where $R^1$ and $R^2$ are H, and $R^1$ and $R^2$ can be phosphodiester linkages, Base can be a nucleobase, and $R^3$ is a functional group described below.

In another view, the UNA monomer main atoms can be drawn in IUPAC notation as follows:

UNA monomer unit

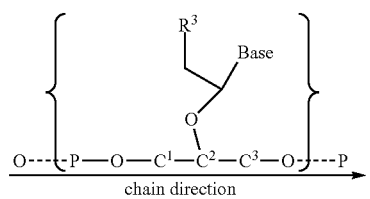

chain direction where the direction of progress of the oligomer chain is from the 1-end to the 3-end of the propane residue.

Examples of a nucleobase include uracil, thymine, cytosine, 5-methylcytosine, adenine, guanine, inosine, and natural and non-natural nucleobase analogues.

In general, because the UNA monomers are not nucleotides, they can exhibit at least four forms in an oligomer. First, a UNA monomer can be an internal monomer in an oligomer, where the UNA monomer is flanked by other monomers on both sides. In this form, the UNA monomer can participate in base pairing when the oligomer is a duplex, for example, and there are other monomers with nucleobases in the duplex.

Examples of UNA monomer as internal monomers flanked at both the propane-1-yl position and the propane-3-yl position, where $R^3$ is —OH, are shown below.

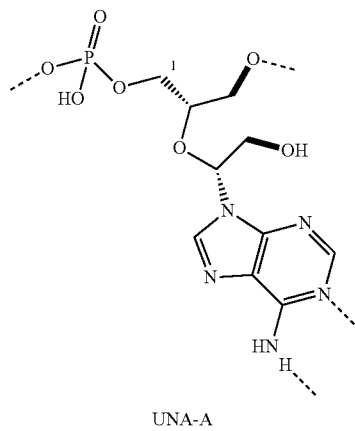

UNA-A

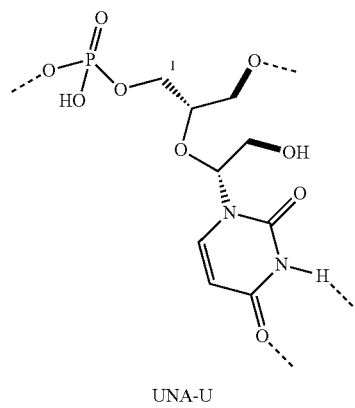

UNA-U

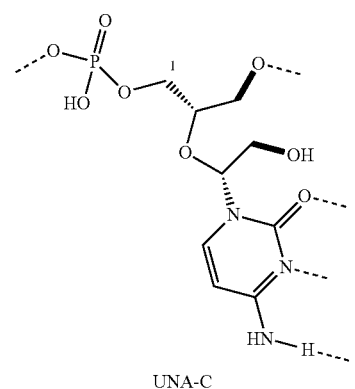

UNA-C

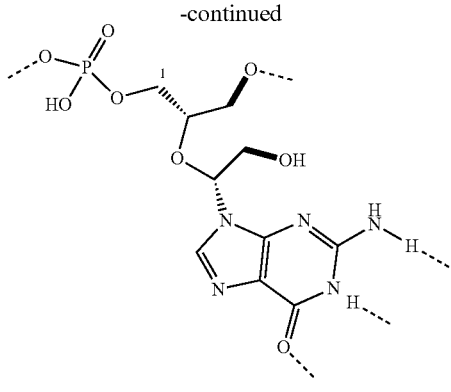

UNA-G

Second, a UNA monomer can be a monomer in an overhang of an oligomer duplex, where the UNA monomer is flanked by other monomers on both sides. In this form, the UNA monomer does not participate in base pairing. Because the UNA monomers are flexible organic structures, unlike nucleotides, the overhang containing a UNA monomer will be a flexible terminator for the oligomer.

A UNA monomer can be a terminal monomer in an overhang of an oligomer, where the UNA monomer is attached to only one monomer at either the propane-1-yl position or the propane-3-yl position. In this form, the UNA monomer does not participate in base pairing. Because the UNA monomers are flexible organic structures, unlike nucleotides, the overhang containing a UNA monomer can be a flexible terminator for the oligomer.

Examples of a UNA monomer as a terminal monomer attached at the propane-3-yl position are shown below.

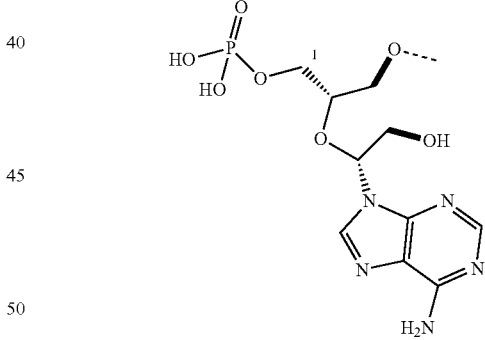

terminal UNA-A

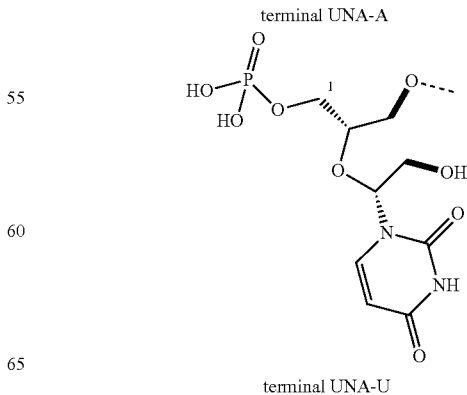

terminal UNA-U

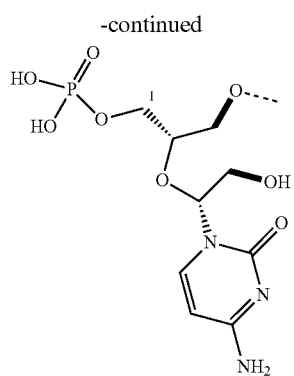

terminal UNA-C

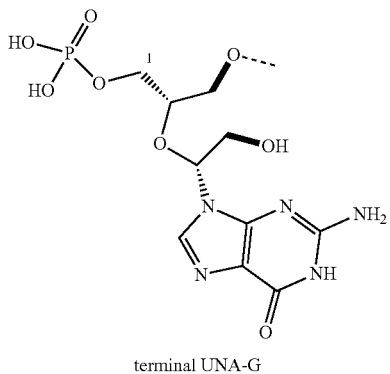

terminal UNA-G

Because a UNA monomer can be a flexible molecule, a UNA monomer as a terminal monomer can assume widely differing conformations. An example of an energy minimized UNA monomer conformation as a terminal monomer attached at the propane-3-yl position is shown below.

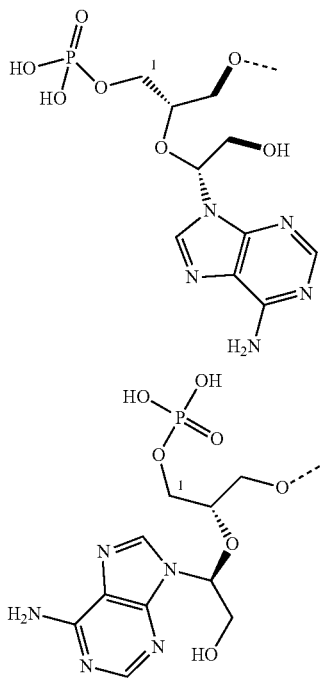

UNA-A Terminal Forms: The Dashed Bond Shows the Propane-3-Yl Attachment

Thus, UNA oligomers having a terminal UNA monomer are significantly different in structure from conventional nucleic acid agents, such as siRNAs. For example, siRNAs may require that terminal monomers or overhangs in a duplex be stabilized. In contrast, the conformability of a terminal UNA monomer can provide UNA oligomers with different properties.

Among other things, the structure of the UNA monomer allows it to be attached to naturally-occurring nucleotides. A UNA oligomer can be a chain composed of UNA monomers, as well as various nucleotides that may be based on naturally-occurring nucleosides.

In some embodiments, the functional group $R^3$ of a UNA monomer can be $OR^4$, $SR^4$, $NR^4{}_2$, —NH(C=O)$R^4$, morpholino, morpholin-1-yl, piperazin-1-yl, or 4-alkanoyl-piperazin-1-yl, where $R^4$ is the same or different for each occurrence, and can be H, alkyl, a cholesterol, a lipid molecule, a polyamine, an amino acid, or a polypeptide.

The UNA monomers are organic molecules. UNA monomers are not nucleic acid monomers or nucleotides, nor are they naturally-occurring nucleosides or modified naturally-occurring nucleosides.

A UNA oligomer of this invention is a synthetic chain molecule. A UNA oligomer of this invention is not a nucleic acid, nor an oligonucleotide.

In some embodiments, as shown above, a UNA monomer can be UNA-A (designated Ã), UNA-U (designated Ũ), UNA-C (designated Č), and UNA-G (designated Ğ).

Designations that may be used herein include mA, mG, mC, and mU, which refer to the 2'-O-Methyl modified ribonucleotides.

Designations that may be used herein include lower case c and u, which refer to the 2'-O-methyl modified ribonucleotides.

Designations that may be used herein include dT, which refers to a 2'-deoxy T nucleotide.

Monomers for UNA Oligomers

As used herein, in the context of oligomer sequences, the symbol X represents a UNA monomer.

As used herein, in the context of oligomer sequences, the symbol N represents any natural nucleotide monomer, or a modified nucleotide monomer.

As used herein, in the context of oligomer sequences, the symbol Q represents a non-natural, modified, or chemically-modified nucleotide monomer.

Examples of non-natural, modified, and chemically-modified nucleotide monomers include 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of non-natural, modified, and chemically-modified nucleotide monomers include 3'-end stabilized nucleotides, 3'-glyceryl nucleotides, 3'-inverted abasic nucleotides, and 3'-inverted thymidine.

Examples of non-natural, modified, and chemically-modified nucleotide monomers include locked nucleic acid nucleotides, 2'-O,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides.

Examples of non-natural, modified, and chemically-modified nucleotide monomers include 2'-amino nucleotides, 2'-O-amino nucleotides, 2'-C-allyl nucleotides, and 2'-O-allyl nucleotides.

Examples of non-natural, modified, and chemically-modified nucleotide monomers include $N^6$-methyladenosine nucleotides.

Examples of non-natural, modified, and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of non-natural, modified, and chemically-modified nucleotide monomers include 2'-O-aminopropyl substituted nucleotides.

Examples of non-natural, modified, and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Some examples of modified nucleotides are given in Saenger, Principles of Nucleic Acid Structure, Springer-Verlag, 1984.

UNA Oligomers

A UNA oligomer of this invention is a chain molecule. A UNA oligomer can be a duplex pair. Thus, a UNA oligomer can have a first strand of the duplex and a second strand of the duplex, which is complementary to the first strand, although up to three mismatches can occur. A UNA oligomer duplex can have overhangs.

Some UNA oligomers are discussed in U.S. Pat. No. 8,314,227, as well as US Patent Publication No. 20110313020 A1.

The target of a UNA oligomer can be a target nucleic acid. In some embodiments, the target can be any mRNA of a subject. A UNA oligomer can be active for gene silencing in RNA interference.

A UNA oligomer may comprise two strands that together provide a duplex. The duplex may be composed of a first strand, which may also be referred to as a passenger strand or sense strand, and a second strand, which may also be referred to as a guide strand or antisense strand.

In some aspects, a UNA oligomer of this invention can have any number of phosphorothioate intermonomer linkages in any position in any strand, or in both strands of a duplex structure.

Examples of UNA oligomers of this invention include duplex pairs, which are in general complementary. Thus, for example, SEQ ID NO:1 can represent a first strand of a duplex and SEQ ID NO:2 can represent a second strand of the duplex, which is complementary to the first strand.

For example, the symbol "N" in the first strand can represent any nucleotide that is complementary to the monomer in the corresponding position in the second strand. Example UNA oligomers of this disclosure are shown with 2-monomer length overhangs, although overhangs of from 1 to 8 monomers, or longer, can be used.

The symbol "X" in a strand or oligomer represents a UNA monomer.

Further, when the oligomer terminates in a UNA monomer, the terminal position has a 1-end, according to the positional numbering shown above, instead of a 5'-end as for a nucleotide, or the terminal position has a 3-end, according to the positional numbering shown above, instead of a 3'-end as for a nucleotide. For example, the UNA oligomer

SEQ ID NO: 1
1-X-N-N-N-N-N-N-N-N-N-N-N-N-N-N-N-N-N-X-X-3

SEQ ID NO: 2
3-X-X-N-N-N-N-N-N-N-N-N-N-X-X-X-X-X-X-X-N-5' has a UNA monomer 1-end on the first strand, a UNA monomer 3-end on the first strand, a UNA monomer 3-end on the second strand, and a nucleotide 5'-end on the second strand.

In some embodiments, a UNA oligomer of this invention can have one or more UNA monomers at the 1-end of the first strand, and one or more UNA monomers at the 3-end of the first strand.

In further embodiments, a UNA oligomer of this invention can have one or more UNA monomers at the 3-end of the second strand.

In certain embodiments, a duplex UNA oligomer of this invention can have one or more UNA monomers at the 1-end of the first strand, one or more UNA monomers at the 3-end of the first strand, and one or more UNA monomers at the 3-end of the second strand.

A UNA oligomer of this invention the oligomer may have a first strand and a second strand, each of the strands independently being 19-23 monomers in length.

In certain embodiments, a UNA oligomer of this invention may have a first strand that is 19-23 monomers in length.

In certain embodiments, a UNA oligomer of this invention may have a duplex region that is 19-21 monomers in length.

In further embodiments, a UNA oligomer of this invention may have a second strand that is 19-23 monomers in length.

In certain embodiments, a UNA oligomer of this invention may have a first strand that is 19 monomers in length, and a second strand that is 21 monomers in length.

In certain embodiments, a UNA oligomer of this invention may have a first strand that is 20 monomers in length, and a second strand that is 21 monomers in length.

In certain embodiments, a UNA oligomer of this invention may have a first strand that is 21 monomers in length, and a second strand that is 21 monomers in length.

In certain embodiments, a UNA oligomer of this invention may have a first strand that is 22 monomers in length, and a second strand that is 21 monomers in length.

A UNA oligomer of this invention for inhibiting gene expression can have a first strand and a second strand, each of the strands being 19-29 monomers in length. The monomers can be UNA monomers and nucleic acid monomers. The oligomer can have a duplex structure of from 14 to 29 monomers in length. The UNA oligomer can be targeted to a target gene and can exhibit reduced off-target effects as compared to a conventional siRNA. In some embodiments, a UNA oligomer of this invention can have a first strand and a second strand, each of the strands being 19-23 monomers in length.

In another aspect, the UNA oligomer may have a blunt end, or may have one or more overhangs. In some embodiments, the first and second strands may be connected with a connecting oligomer in between the strands, and form a duplex region with a connecting loop at one end.

In certain embodiments, an overhang can be one or two monomers in length.

A UNA oligomer can mediate cleavage of a target nucleic acid in a cell. In some processes, the second strand of the UNA oligomer, at least a portion of which can be complementary to the target nucleic acid, can act as a guide strand that can hybridize to the target nucleic acid.

The second strand can be incorporated into an RNA Induced Silencing Complex (RISC).

A UNA oligomer of this disclosure may comprise naturally-occurring nucleic acid nucleotides, and modifications thereof that are compatible with gene silencing activity.

In some aspects, a UNA oligomer is a double stranded construct molecule that is able to inhibit gene expression.

As used herein, the term strand refers to a single, contiguous chain of monomers, the chain having any number of internal monomers and two end monomers, where each end monomer is attached to one internal monomer on one side, and is not attached to a monomer on the other side, so that it ends the chain.

The monomers of a UNA oligomer may be attached via phosphodiester linkages, phosphorothioate linkages, gapped linkages, and other variations.

In some embodiments, a UNA oligomer can include mismatches in complementarity between the first and second strands. In other embodiments, a UNA oligomer may have 1, or 2, or 3 mismatches. The mismatches may occur at any position in the duplex region.

The target of a UNA oligomer can be a target nucleic acid of a target gene.

A UNA oligomer may have one or two overhangs outside the duplex region. The overhangs can be an unpaired portion at the end of the first strand or second strand. The lengths of the overhang portions of the first and second strands can be the same or different.

A UNA oligomer may have at least one blunt end. A blunt end does not have an overhang portion, and the duplex region at a blunt end terminates at the same position for both the first and second strands.

A UNA oligomer can be RISC length, which means that it has a duplex length of less than 25 base pairs.

In certain embodiments, a UNA oligomer can be a single strand that folds upon itself and hybridizes to itself to form a double stranded region having a connecting loop.

Examples of UNA oligomer structures having reduced off-target effects are shown in Table 1.

In some embodiments, a UNA oligomer having reduced off-target effects can have a UNA monomer at the first position at the 1 end of the first strand, also called the passenger strand, and one or both of the last two positions from the 3 end of the first strand, as well as one or both of the last two positions from the 3 end of the second strand, also called the guide strand. For example, SEQ ID NOs:3 and 4 in Table 1, in which both of the last two positions from the 3 end of the first strand, and both of the last two positions from the 3 end of the second strand are UNA monomers.

In some embodiments, a UNA oligomer having reduced off-target effects can have a UNA monomer at the first position at the 1 end of the first strand, and one or both of the last two positions from the 3 end of the first strand. For example, SEQ ID NOs:5 and 6 in Table 1, in which both of the last two positions from the 3 end of the first strand are UNA monomers.

In some embodiments, a UNA oligomer having reduced off-target effects can have a UNA monomer at the first position at the 1 end of the first strand, also called the passenger strand, and one or more of the last two positions from the 3 end of the second strand. For example, SEQ ID NOs:7 and 8 in Table 1, in which both of the last two positions from the 3 end of the second strand are UNA monomers.

In some embodiments, a UNA oligomer having reduced off-target effects can have a UNA monomer at the first position at the 1 end of the first strand. For example, SEQ ID NOs:9 and 10 in Table 1.

In some embodiments, a UNA oligomer having reduced off-target effects can have a UNA monomer at one or more of the last two positions from the 3 end of the first strand, as well as one or more of the last two positions from the 3 end of the second strand. For example, SEQ ID NOs:11 and 12 in Table 1, in which both of the last two positions from the 3 end of the first strand, and both of the last two positions from the 3 end of the second strand are UNA monomers.

In some embodiments, in addition to having one or more UNA monomers at any of the positions described above, a UNA oligomer having reduced off-target effects can have a UNA monomer in the seed region at any one or more of positions 2-8 from the 5' end of the second strand.

TABLE 1

UNA oligomers having reduced off-target effects

| SEQ ID NO: | OLIGOMER |
|---|---|
| 3 | 1-X·N·N·N·N·N·N·N·N·N.N·N·N·N·N·N·N·N·X·X-3 |
| 4 | 3-X·X·N·N·N·N·N·N·N·N·N·N·N·N·N·N·N·N·N-5' |
| 5 | 1-X·N·N·N·N·N·N·N·N·N.N·N·N·N·N·N·N·N·X·X-3 |
| 6 | 3-N·N·N·N·N·N·N·N·N·N·N·N·N·N·N·N·N·N·N-5' |
| 7 | 1-X·N·N·N·N·N·N·N·N·N.N·N·N·N·N·N·N·N·N·N-3 |
| 8 | 3-X·X·N·N·N·N·N·N·N·N·N·N·N·N·N·N·N·N·N-5' |
| 9 | 1-X·N·N·N·N·N·N·N·N·N.N·N·N·N·N·N·N·N·X·X-3 |
| 10 | 3-N·N·N·N·N·N·N·N·N·N·N·N·N·N·N·N·N·N·N-5' |
| 11 | 1-X·N·N·N·N·N·N·N·N·N.N·N·N·N·N·N·N·N·X·X-3 |
| 12 | 3-X·X·N·N·N·N·N·N·N·N·N·N·N·N·N·N·N·N·N-5' |
| 13 | 1-N·N·N·N·N·N·N·N·N·N.N·N·N·N·N·N·N·N·X·X-3 |
| 14 | 3-N·N·N·N·N·N·N·N·N·N·N·N·N·N·N·N·N·N·N-5' |
| 15 | 1-N·N·N·N·N·N·N·N·N·N.N·N·N·N·N·N·N·N·N·N-3 |
| 16 | 3-X·X·N·N·N·N·N·N·N·N·N·N·N·N·N·N·N·N·N-5' |

In some embodiments, a UNA oligomer having reduced off-target effects can have a UNA monomer at the first Examples of UNA oligomer structures having reduced off-target effects are shown in Table 2.

TABLE 2

UNA oligomers having reduced off-target effects

| SEQ ID NO: | OLIGOMER |
|---|---|
| 17 | 1-X·N·N·N·N·N·N·N·N·N.N·N·N·N·N·N·N·N·X·X-3 |
| 18 | 3-X·X·N·N·N·N·N·N·N·N·N·N·X·X·X·X·X·X·N-5' |
| 19 | 1-X·N·N·N·N·N·N·N·N·N.N·N·N·N·N·N·N·N·X-3 |
| 20 | 3-N·N·N·N·N·N·N·N·N·N·N·N·X·X·X·X·X·X·N-5' |
| 21 | 1-X·N·N·N·N·N·N·N·N·N.N·N·N·N·N·N·N·N·N-3 |
| 22 | 3-X·X·N·N·N·N·N·N·N·N·N·N·X·X·X·X·X·X·N-5' |
| 23 | 1-X·N·N·N·N·N·N·N·N·N.N·N·N·N·N·N·N·N·N-3 |
| 24 | 3-N·N·N·N·N·N·N·N·N·N·N·N·X·X·X·X·X·X·N-5' |
| 25 | 1-N·N·N·N·N·N·N·N·N·N.N·N·N·N·N·N·N·X·X-3 |
| 26 | 3-N·N·N·N·N·N·N·N·N·N·N·N·X·X·X·X·X·X·N-5' |
| 27 | 1-N·N·N·N·N·N·N·N·N·N.N·N·N·N·N·N·N·N·X-3 |
| 28 | 3-X·X·N·N·N·N·N·N·N·N·N·N·X·X·X·X·X·X·N-5' |
| 29 | 1-N·N·N·N·N·N·N·N·N·N.N·N·N·N·N·N·N·N·N-3 |
| 30 | 3-X·X·N·N·N·N·N·N·N·N·N·N·X·X·X·X·X·X·N-5' |
| 31 | 1-N·N·N·N·N·N·N·N·N·N.N·N·N·N·N·N·N·N·N-3 |
| 32 | 3-N·N·N·N·N·N·N·N·N·N·N·N·X·X·X·X·X·X·N-5' |

Methods for Treating Amyloidosis

Methods of this invention include the treatment and prevention of TTR-related amyloidosis in mammalian subjects, with reduced off-target effects.

In the methods of this invention, a subject in need of treatment or prevention can be administered an effective amount of a UNA oligomer. A subject can be a human or mammal.

The subject may have TTR-related amyloidosis, also known as ATTR.

In particular, a subject can have a V30M gene. The methods of this invention can reduce V30M TTR in the subject, with reduced off-target effects.

In some embodiments, a method of this invention can reduce TTR, or V30M TTR in the subject by at least 10%, as compared to control, with reduced off-target effects. In certain embodiments, TTR or V30M TTR in the subject can be reduced by at least 20%, or 30%, or 50%, as compared to control, with reduced off-target effects.

An effective amount of a UNA oligomer of this invention can be a dose ranging from 0.001 mg/kg to 50.0 mg/kg.

In the methods of this invention, TTR mRNA expression can be reduced in a subject for at least 5 days. In certain embodiments, TTR mRNA expression can be reduced in a subject for at least 10 days, or 15 days.

In the methods of this invention, peripheral neuropathy or autonomic neuropathy in the subject can be reduced.

In the methods of this invention, peripheral neuropathy or autonomic neuropathy in the subject can be reduced. In some embodiments, a subject may undergo reduced lower extremity weakness, reduced pain, or improved sensation. Methods of this invention can reduce occurrence of vitreous opacities in the subject.

In the methods of this disclosure, the administration of a UNA oligomer may not result in an inflammatory response.

In further embodiments, this invention includes methods for inhibiting expression of a TTR gene in a cell, by treating the cell with a UNA oligomer.

In additional embodiments, this invention includes methods for inhibiting expression of a TTR gene in a mammal, by administering to the mammal a composition containing a UNA oligomer.

Pharmaceutical Compositions

In some aspects, this invention provides pharmaceutical compositions containing a UNA oligomer and a pharmaceutically acceptable carrier.

A pharmaceutical composition can be capable of local or systemic administration. In some aspects, a pharmaceutical composition can be capable of any modality of administration. In certain aspects, the administration can be intravenous, subcutaneous, pulmonary, intramuscular, intraperitoneal, dermal, oral, or nasal administration.

Embodiments of this invention include pharmaceutical compositions containing a UNA oligomer in a lipid formulation.

In some embodiments, a pharmaceutical composition may comprise one or more lipids selected from cationic lipids, anionic lipids, sterols, pegylated lipids, and any combination of the foregoing.

In certain embodiments, a pharmaceutical composition can be substantially free of liposomes.

In further embodiments, a pharmaceutical composition can include liposomes.

In additional embodiments, a pharmaceutical composition can contain a UNA oligomer within a viral or bacterial vector.

A pharmaceutical composition of this disclosure may include carriers, diluents or excipients as are known in the art. Examples of pharmaceutical compositions are described, for example, in Remington's Pharmaceutical Sciences, Mack Publishing Co. (A. R. Gennaro ed. 1985).

Examples of excipients for a pharmaceutical composition include antioxidants, suspending agents, dispersing agents, preservatives, buffering agents, tonicity agents, and surfactants.

EXAMPLES

Example 1

This example shows that UNA oligomers dramatically reduce off target activity of the passenger strand in gene silencing by RNA interference. The reduction in passenger strand off target activity can depend on the positioning of various UNA monomers in the oligomer. In this example, it is shown that the presence of a combination of UNA monomers in three positions in a UNA oligomer, more specifically, in the passenger strand at the 5' end and at the 3' end, as well as in the guide strand at the 3' end, greatly reduced off target knockdown activity by the passenger strand.

UNA oligomers targeted to ApoCIII having reduced off-target effects are shown in Table 3. As used herein, a duplex oligomer is represented with the passenger strand above, and the guide strand below. The end group numbering will depend on the identity of the terminal monomer, as described above.

TABLE 3

UNA oligomers ATX98 and ATX100

| SEQ ID NO: | | OLIGOMER |
|---|---|---|
| 33 | ATX98 | 1-ÃAAAGGGACAGUAUUCUCAÛmU-3' |
| 34 | | 3'-mUÛUUUUCCCUGUCAUAAGAGU-5' |
| 35 | ATX100 | 1-ĈAAUAAAGCUGGACAAGAAÛmU-3' |
| 36 | | 3'-mUÛGUUAUUUCGACCUGUUCUU-5' |

FIG. 1 shows that a UNA oligomer demonstrated surprisingly reduced off target activity for ApoCIII mRNA expression in a dual Luciferase reporter assay using PSICHECK-2 VECTOR (Promega). In particular, UNA oligomer ATX98 having UNA monomers in the passenger strand located at the 5' end position 1 (Ã) and at position 20 (Ũ), as well as in the guide strand at position 20 (Ũ) had greatly reduced off target knockdown activity by the passenger strand (PSCM) as compared to a comparable UNA oligomer ATS98, which did not have a UNA monomer in the passenger strand located at the 5' end position 1 (Ã).

The IC50 for the passenger strand of ATS98 was 1.57, and the IC50 for the passenger strand of ATX98 was 397. Thus, the UNA oligomer ATX98 had over 250-fold reduced off target knockdown, as measured by the ratio of IC50s. This dramatic reduction in off target knockdown can be attributed to the presence of a combination of UNA monomers in three positions in the UNA oligomer: at the 5' end and at the 3' end of the passenger strand, as well as in the guide strand at the 3' end.

Figure 2:
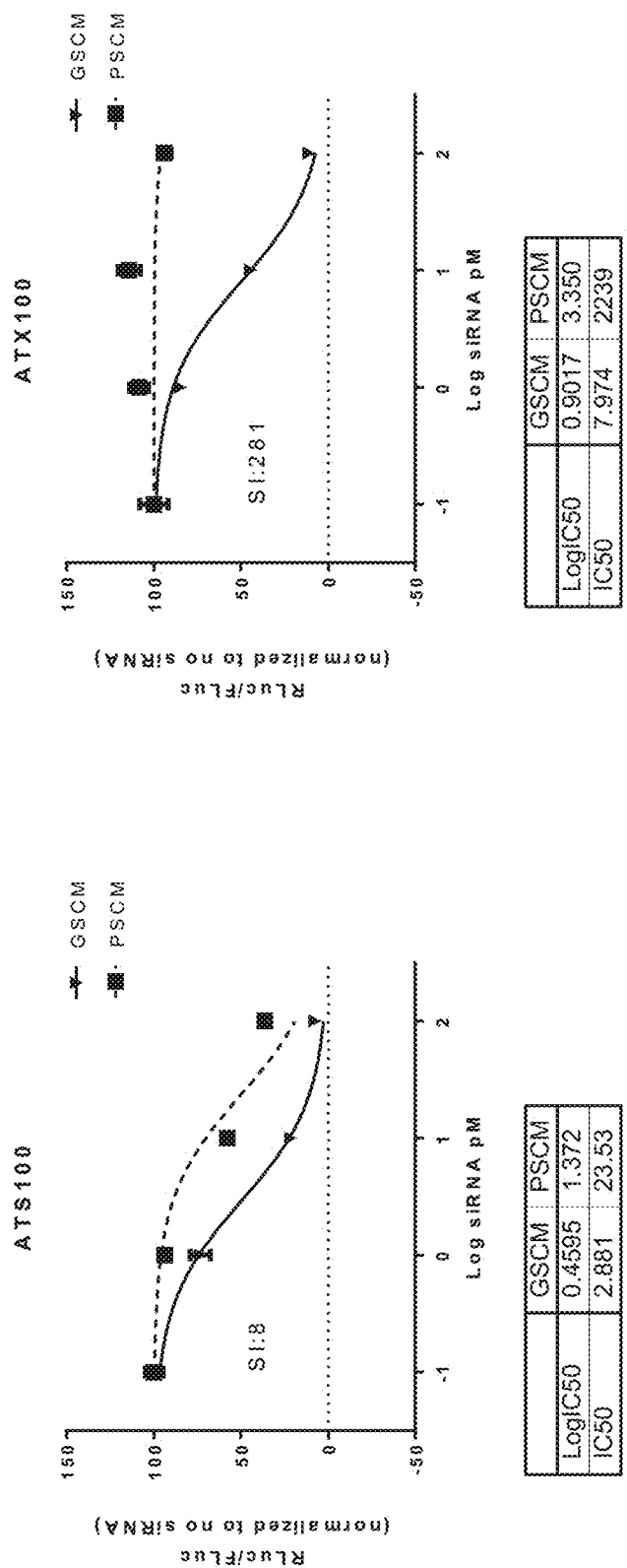
FIG. 2 shows that a UNA oligomer demonstrated surprisingly reduced off target activity for ApoCIII mRNA expression in a dual Luciferase reporter assay using PSICHECK-2 VECTOR. In particular, UNA oligomer ATX100 having UNA monomers in the passenger strand located at the 5' end position 1 (Č) and at position 20 (Ũ), as well as in the guide strand at position 20 (Ũ) had greatly reduced off target knockdown activity by the passenger strand (PSCM) as compared to a comparable UNA oligomer ATS100, which did not have a UNA monomer in the passenger strand located at the 5' end position 1 (Č). The UNA oligomer ATX100 had almost 100-fold reduced off target knockdown.

FIG. 2 shows that UNA oligomer ATX100 demonstrated surprisingly reduced off target activity for ApoCIII mRNA expression in a dual Luciferase reporter assay using PSICHECK-2 VECTOR. ATX100 had UNA monomers in the passenger strand located at the 5' end position 1 (Č) and at position 20 (Ũ), as well as in the guide strand at position 20 (Ũ), and had greatly reduced off target knockdown activity by the passenger strand (PSCM) as compared to a comparable UNA oligomer ATS100, which did not have a UNA monomer in the passenger strand located at the 5' end position 1 (Č).

The IC50 for the passenger strand of ATS100 was 23.5, and the IC50 for the passenger strand of ATX100 was 2239. Thus, the UNA oligomer ATX100 had almost 100-fold reduced off target knockdown, as measured by the ratio of IC50s. This dramatic reduction in off target knockdown can be attributed to the presence of a combination of UNA monomers in three positions in the UNA oligomer: at the 5' end and at the 3' end of the passenger strand, as well as in the guide strand at the 3' end.

Example 2

Figure 3:
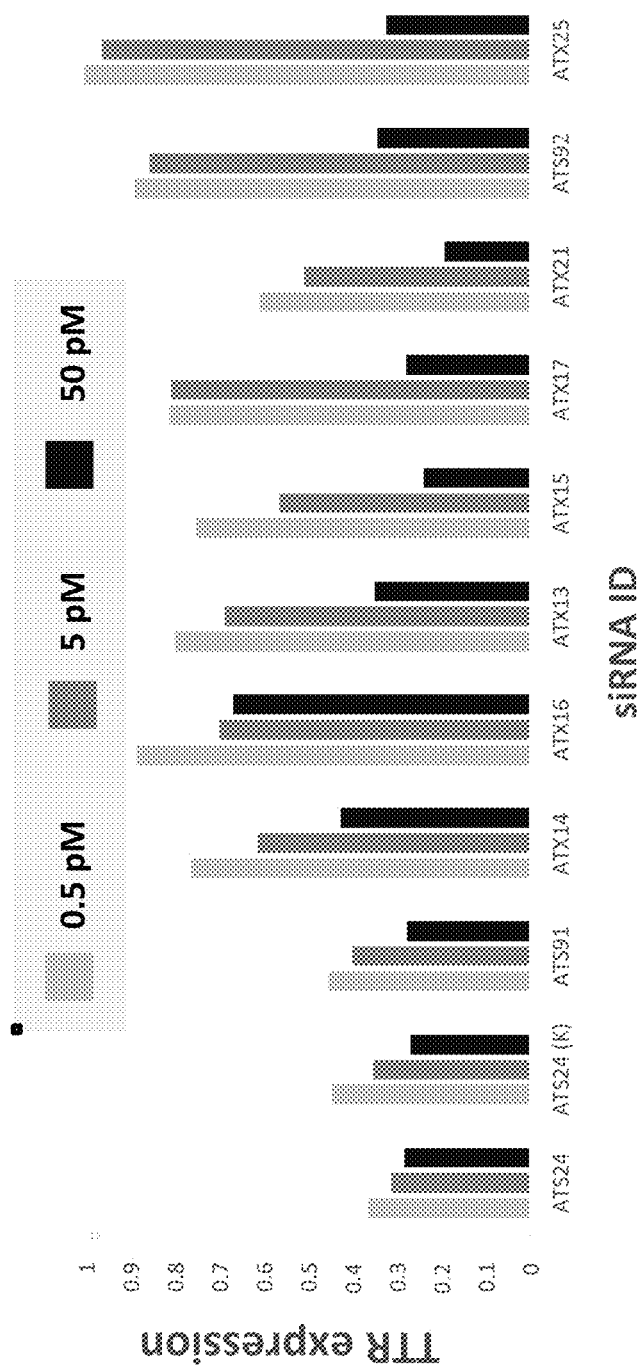
FIG. 3 shows that certain UNA oligomers had at least comparable knockdown levels of activity to conventional siRNAs for TTR mRNA expression. In particular, UNA oligomer ATX13 having a UNA monomer in the first strand located at the 5' end, and UNA oligomer ATX15 having a UNA monomer in the first strand located at the 5' end and two UNA monomers in the second strand located at the 3' end in the $20^{th}$ and $21^{st}$ positions counting from the 5' end, had at least comparable knockdown levels of activity as compared to conventional siRNA ATS-91. Further, UNA oligomer ATX21 having a UNA monomer in the first strand located at the 5' end, one UNA monomer in the first strand located at the 3' end in the $20^{th}$ position counting from the 5' end, and one UNA monomer in the second strand located at the 3' end in the $20^{th}$ position counting from the 5' end, had at least comparable knockdown levels of activity as compared to conventional siRNA ATS-91. Moreover, in a head-to-head comparison, ATX25 having a UNA monomer in the first strand located at the 5' end, one UNA monomer in the first strand located at the 3' end in the $20^{th}$ position counting from the 5' end, and one UNA monomer in the second strand located at the 3' end in the $20^{th}$ position counting from the 5' end, had at least comparable knockdown levels of activity as compared to conventional siRNA ATS-92.

FIG. 3 shows that certain UNA oligomers had at least comparable knockdown levels of activity to conventional siRNAs for TTR mRNA expression. ATX13, ATX14, ATX15, ATX16, ATX17, ATX21 and ATX25 were targeted to the 3'-UTR of human TTR, and therefore were targeted to both wild-type V30V and V30M mutant TTR.

In particular, UNA oligomer ATX13 having a UNA monomer in the first strand located at the 1 (5') end, and UNA oligomer ATX15 having a UNA monomer in the first strand located at the 1 (5') end and two UNA monomers in the second strand located at the 3 (3') end in the $20^{th}$ and $21^{st}$ positions counting from the 5' end, had at least comparable knockdown levels of activity as compared to conventional siRNA ATS-91.

Further, UNA oligomer ATX21 having a UNA monomer in the first strand located at the 1 (5') end, one UNA monomer in the first strand located at the 3 (3') end in the $20^{th}$ position counting from the 5' end, and one UNA monomer in the second strand located at the 3 (3') end in the $20^{th}$ position counting from the 5' end, had at least comparable knockdown levels of activity as compared to conventional siRNA ATS-91.

Moreover, in a head-to-head comparison, ATX25 having a UNA monomer in the first strand located at the 1 (5') end, one UNA monomer in the first strand located at the 3 (3') end in the $20^{th}$ position counting from the 1 end, and one UNA monomer in the second strand located at the 3 (3') end in the $20^{th}$ position counting from the 5' end, had at least comparable knockdown levels of activity as compared to conventional siRNA ATS-92.

FIG. 4 shows the structures of UNA oligomers ATX13, ATX15 and ATX21.

Example 3

Figure 5:
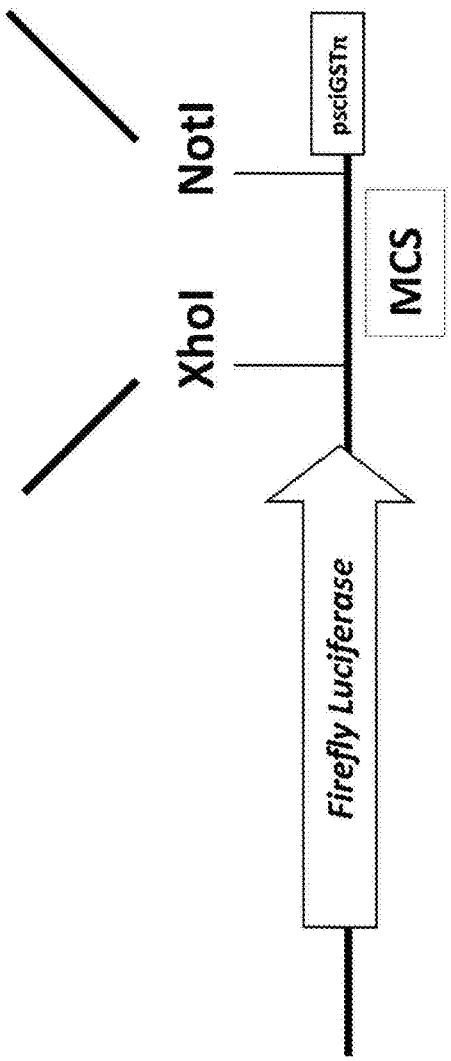
FIG. 5 shows the protocol for measuring off-target (OT) effects. A dual Luciferase reporter assay using PSICHECK-2 VECTOR (Promega) was established to quantitate off-target effects. For each measurement, 4 plasmids were constructed: guide strand GSCM and guide strand GSSM for second strand or antisense knockdown, and passenger strand PSCM and passenger strand PSSM for first strand or sense strand knockdown. The reporter plasmid was co-transfected with UNA oligomer into HeLa cells. In this system. If the UNA oligomer binds to the target sequence inserted in 3-UTR of luciferase, then the chemiluminescent signal is reduced or disappeared.

FIG. 5 shows the protocol for measuring off-target (OT) effects. A Luciferase reporter assay using PSICHECK vector was established. For each measurement, 4 plasmids were constructed: guide strand GSCM and guide strand GSSM for second strand or antisense knockdown, and passenger strand PSCM and passenger strand PSSM for first strand or sense strand knockdown. The reporter plasmid was co-transfected with UNA oligomer into HeLa cells. In this system, if the UNA oligomer binds to the target sequence inserted in 3-UTR of luciferase, then the chemiluminescent signal is reduced or disappeared.

Example 4

FIG. 6 shows the structures of UNA oligomers that were used in a head-to-head comparison against conventional siRNAs for knockdown levels. The UNA oligomers were tiled around position 628 in the TTR mRNA region from position 625 to position 651. Five UNA oligomers were prepared, namely ATX25, ATX37, ATX21, ATX38 and ATX39. These UNA oligomers were tested for off-target effects as compared to conventional siRNAs targeted to the same positions.

Example 5

FIG. 7 shows the structure of some embodiments of UNA oligomers that have reduced off-target effects.

Figure 8:
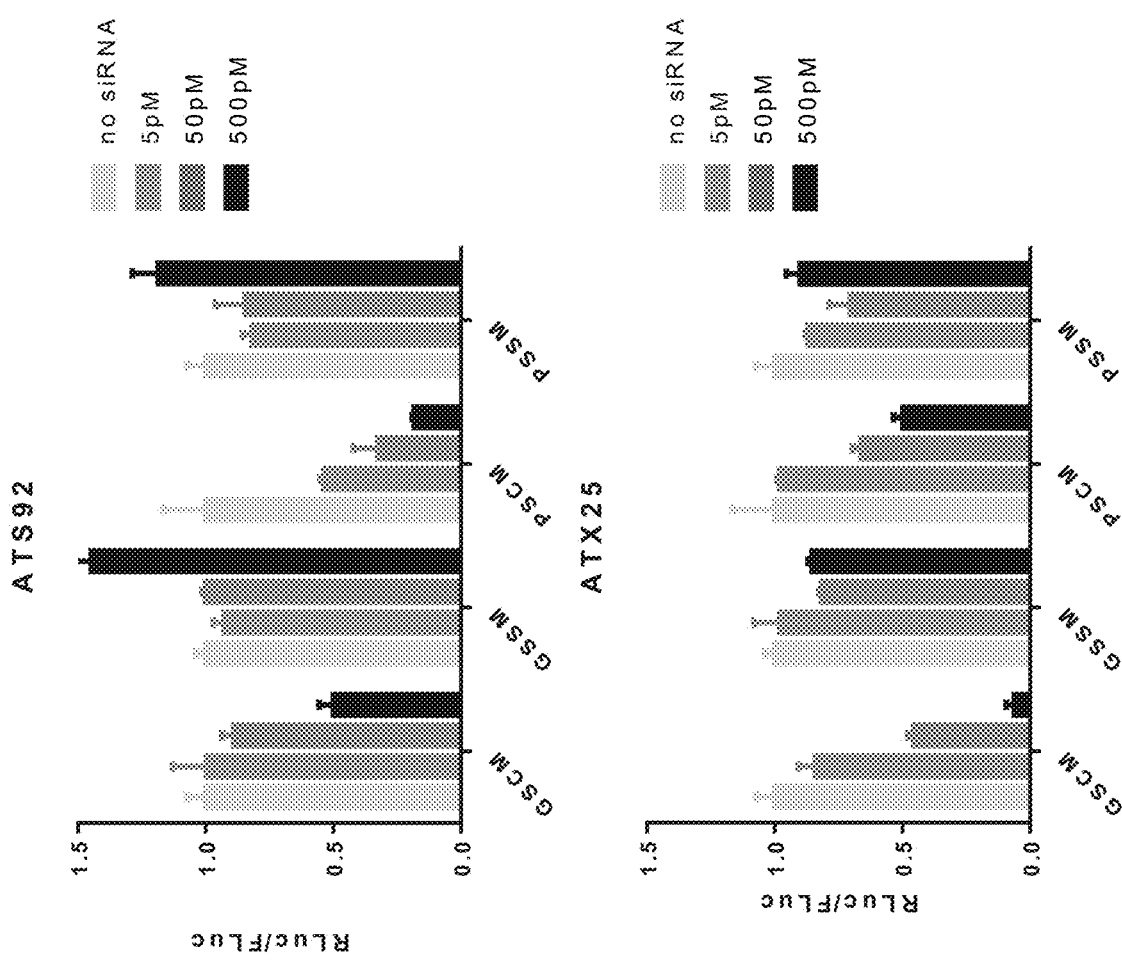
FIG. 8 shows the results of a head-to-head comparison of UNA oligomer ATX25 against conventional siRNA ATS92 for off-target effects in knockdown of TTR expression. The UNA oligomer ATX25 had increased knockdown over the conventional siRNA (GSCM). Surprisingly, the UNA oligomer ATX25 had reduced off-target knockdown compared to the conventional siRNA (PSCM).

FIG. 8 shows the results of a head-to-head comparison of UNA oligomer ATX25 against conventional siRNA ATS92 for off-target effects in knockdown of TTR expression. The UNA oligomer ATX25 had increased knockdown over the conventional siRNA (GSCM). Surprisingly, the UNA oligomer ATX25 had reduced off-target knockdown compared to the conventional siRNA (PSCM).

Example 6

Figure 9:
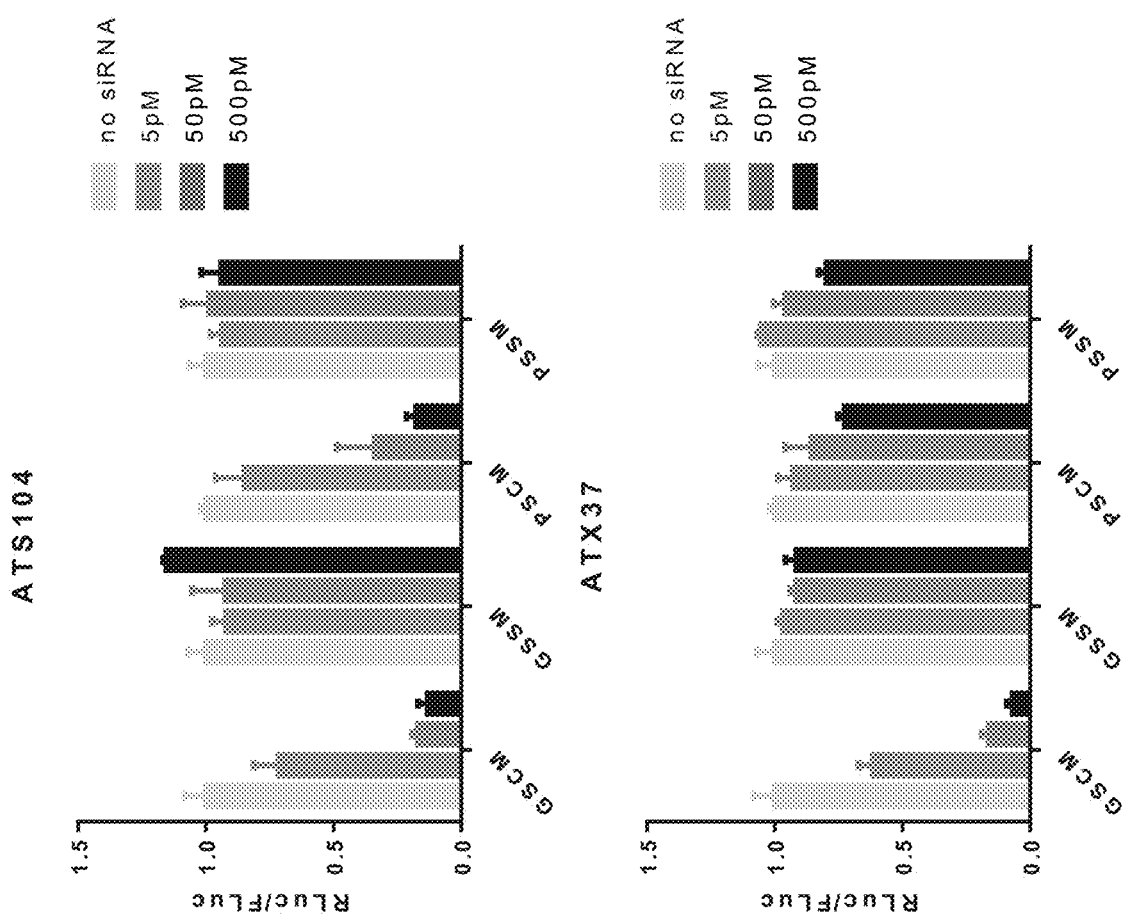
FIG. 9 shows the results of a head-to-head comparison of UNA oligomer ATX37 against conventional siRNA ATS104 for off-target effects in knockdown of TTR expression. The UNA oligomer ATX37 had increased knockdown over the conventional siRNA (GSCM). Surprisingly, the UNA oligomer ATX37 had substantially reduced off-target knockdown compared to the conventional siRNA (PSCM).

FIG. 9 shows the results of a head-to-head comparison of UNA oligomer ATX37 against conventional siRNA ATS104 for off-target effects in knockdown of TTR expression. The UNA oligomer ATX37 had increased knockdown over the conventional siRNA (GSCM). Surprisingly, the UNA oligomer ATX37 had substantially reduced off-target knockdown compared to the conventional siRNA (PSCM).

Example 7

Figure 10:
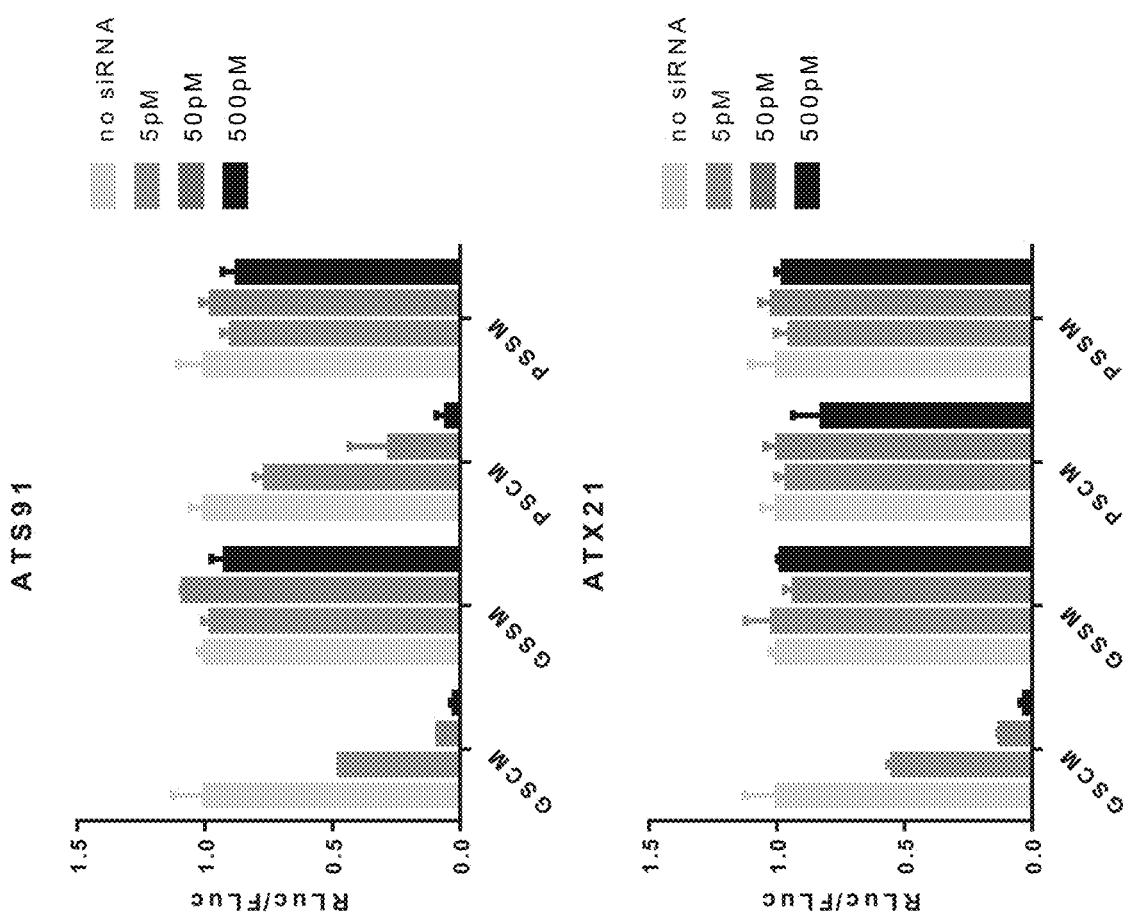
FIG. 10 shows the results of a head-to-head comparison of UNA oligomer ATX21 against conventional siRNA ATS91 for off-target effects in knockdown of TTR expression. The UNA oligomer ATX21 had comparable knockdown to the conventional siRNA (GSCM). Surprisingly, the UNA oligomer ATX21 had substantially reduced off-target knockdown compared to the conventional siRNA (PSCM).

FIG. 10 shows the results of a head-to-head comparison of UNA oligomer ATX21 against conventional siRNA ATS91 for off-target effects in knockdown of TTR expression. The UNA oligomer ATX21 had comparable knockdown to the conventional siRNA (GSCM). Surprisingly, the UNA oligomer ATX21 had substantially reduced off-target knockdown compared to the conventional siRNA (PSCM).

Example 8

Figure 11:
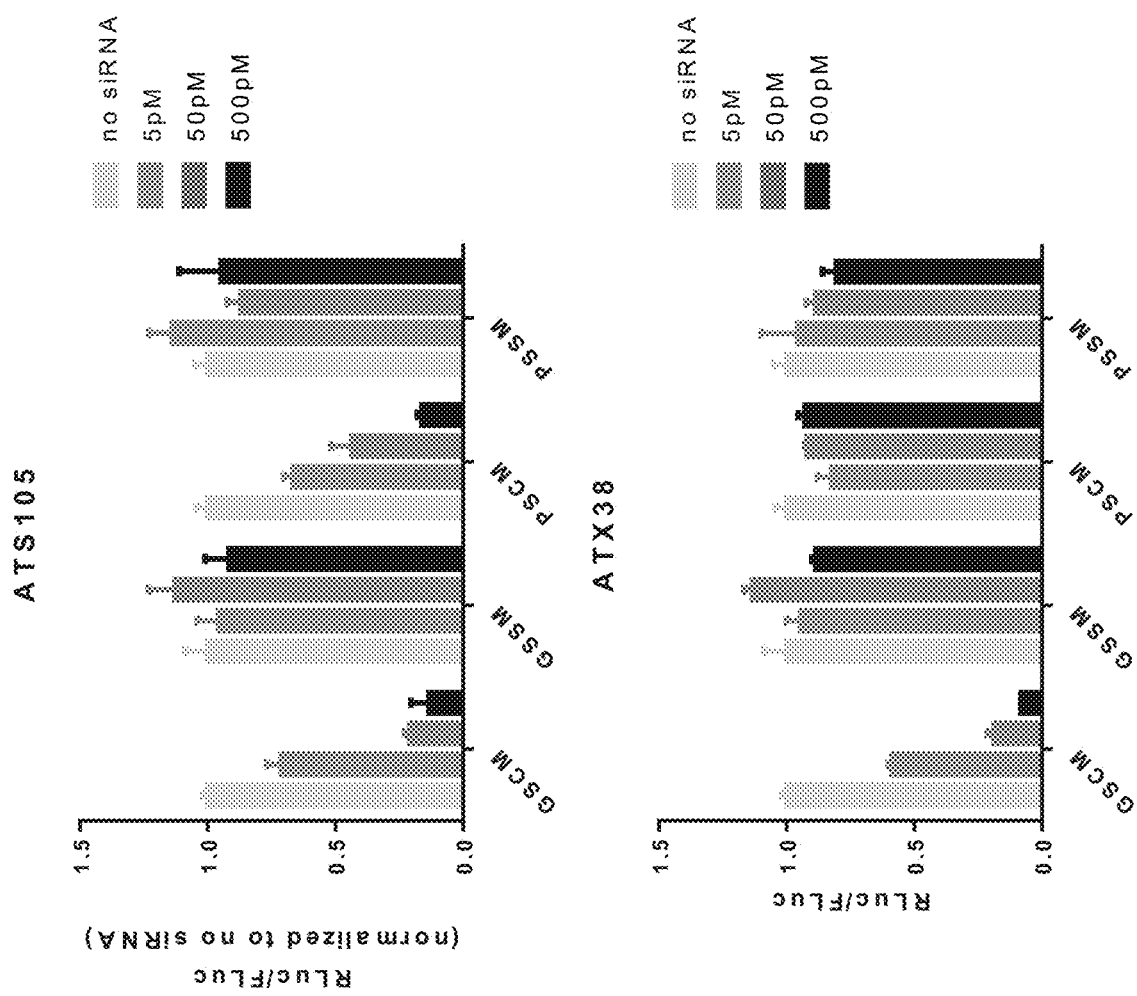
FIG. 11 shows the results of a head-to-head comparison of UNA oligomer ATX38 against conventional siRNA ATS105 for off-target effects in knockdown of TTR expression. The UNA oligomer ATX38 had increased knockdown compared the conventional siRNA (GSCM). Surprisingly, the UNA oligomer ATX38 had substantially reduced off-target knockdown compared to the conventional siRNA (PSCM).

FIG. 11 shows the results of a head-to-head comparison of UNA oligomer ATX38 against conventional siRNA ATS105 for off-target effects in knockdown of TTR expression. The UNA oligomer ATX38 had increased knockdown compared the conventional siRNA (GSCM). Surprisingly, the UNA oligomer ATX38 had substantially reduced off-target knockdown compared to the conventional siRNA (PSCM).

Example 9

Figure 12:
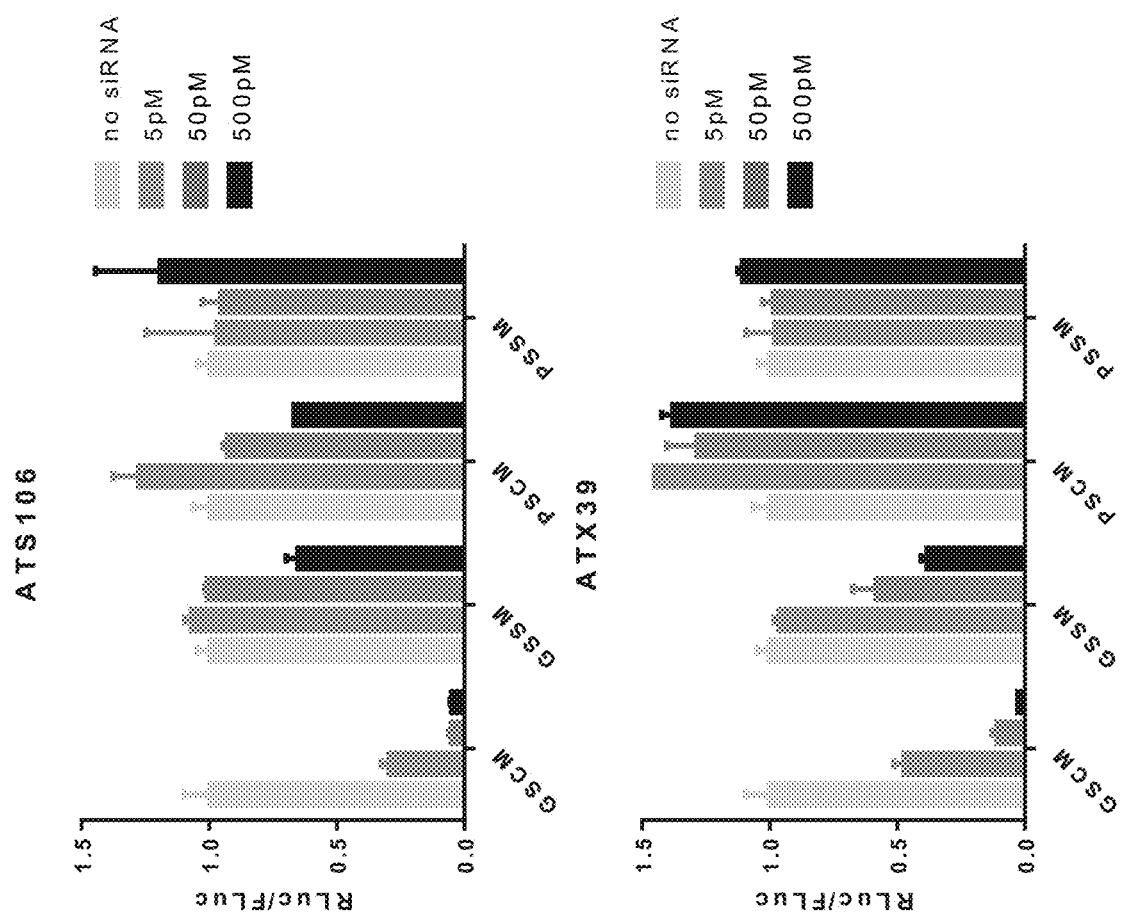
FIG. 12 shows the results of a head-to-head comparison of UNA oligomer ATX39 against conventional siRNA ATS106 for off-target effects in knockdown of TTR expression. The UNA oligomer ATX39 had comparable knockdown compared to the conventional siRNA (GSCM). Surprisingly, the UNA oligomer ATX39 had substantially reduced off-target knockdown compared to the conventional siRNA (PSCM).

FIG. 12 shows the results of a head-to-head comparison of UNA oligomer ATX39 against conventional siRNA ATS106 for off-target effects in knockdown of TTR expression. The UNA oligomer ATX39 had comparable knockdown compared to the conventional siRNA (GSCM). Surprisingly, the UNA oligomer ATX39 had substantially reduced off-target knockdown compared to the conventional siRNA (PSCM).

Example 10

This example shows unexpected reductions in off target activity for UNA oligomers. The reduction in passenger strand off target activity depends on the positioning of various UNA monomers in the oligomer. In this example, it is shown that the presence of a combination of UNA monomers in three positions in a UNA oligomer, more specifically, in the passenger strand at the 1 end and at the 3 (3') end, as well as in the guide strand at the 3 (3') end, provides unexpectedly reduced off target knockdown activity by the passenger strand.

Figure 13:
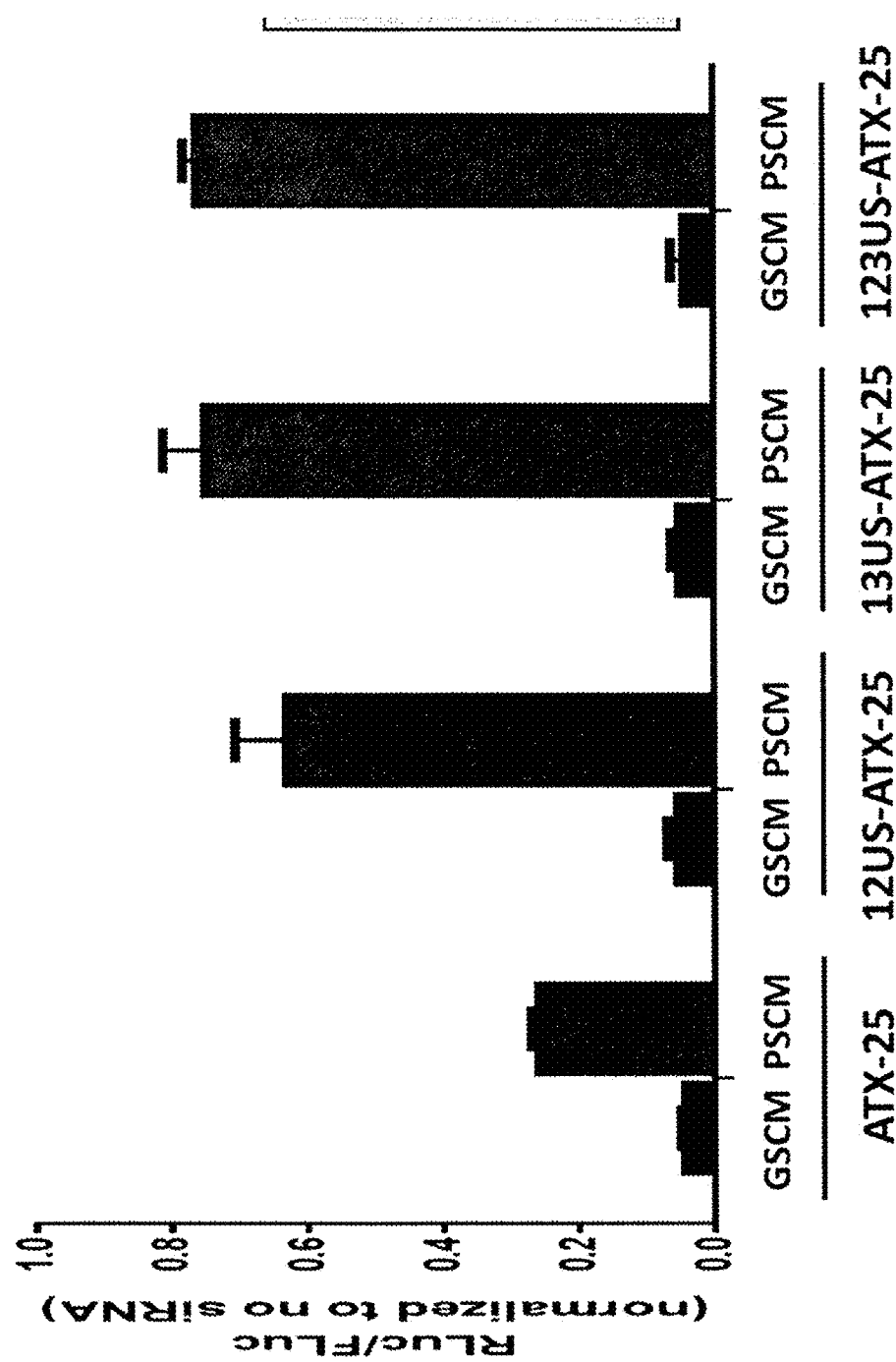
FIG. 13 shows that certain UNA oligomers demonstrated unexpectedly reduced off-target effects. In particular, it is shown that the presence of a combination of UNA monomers in three positions in a UNA oligomer, more specifically, in the passenger strand at the 5' end and at the 3' end, as well as in the guide strand at the 3' end, provides unexpectedly reduced off target knockdown activity by the passenger strand.

The UNA oligomers of FIG. 13, based on ATX25 targeted to TTR having reduced off-target effects, are shown in Table 4.

TABLE 4

UNA oligomers based on ATX25

| SEQ ID NO: | | OLIGOMER |
|---|---|---|
| 37 | 1U- | 1-ÃUGUAACCAAGAGUAUUCCŨmU-3' |
| 38 | ATX25 | 3'-mUŨUACAUUGGUUCUCAUAAGG-5' |
| 39 | 12U- | 1-ÃŨGUAACCAAGAGUAUUCCŨmU-3' |
| 40 | ATX25 | 3'-mUŨUACAUUGGUUCUCAUAAGG-5' |
| 41 | 13U- | 1-ÃUG̃UAACCAAGAGUAUUCCŨmU-3' |
| 42 | ATX25 | 3'-mUŨUACAUUGGUUCUCAUAAGG-5' |
| 43 | 123U- | 1-ÃŨG̃UAACCAAGAGUAUUCCŨmU-3' |
| 44 | ATX25 | 3'-mUŨUACAUUGGUUCUCAUAAGG-5' |

FIG. 13 shows that certain UNA oligomers based on ATX25 targeted to TTR demonstrated unexpectedly reduced off-target effects. A dual Luciferase reporter assay using PSICHECK-2 VECTOR (Promega) was used. In particular, UNA oligomer 1U-ATX25 having UNA monomers in the passenger strand located at the 5' end position 1 (Ã) and at position 20 (Ũ), as well as in the guide strand at position 20 (Ũ) had reduced off target knockdown activity by the passenger strand (PSCM). Surprisingly, for 12U-ATX25, the addition of a UNA monomer to the structure of the oligomer, located at the 5' end position 2 (Ũ) provided a 4-fold reduction of the off target knockdown activity by the passenger strand (PSCM). Also, for 13U-ATX25, the addition of a UNA monomer to the structure of the oligomer, located at the 5' end position 3 (G̃) provided a 6-fold reduction of the off target knockdown activity by the passenger strand (PSCM). Further, the addition of UNA monomers to the structure of the oligomer, located at the 5' end position 2 (Ũ) and position 3 (G̃) provided a 7-fold reduction of the off target knockdown activity by the passenger strand (PSCM). The results from FIG. 13 are recapitulated in Table 5.

TABLE 5

Off Target Activity of UNA oligomers based on ATX25

| UNA oligomer | IC50 (pM) Guide GSCM | IC50 (pM) Passenger PSCM |
|---|---|---|
| 1U-ATX-25 | 18 | 211 |
| 12U-ATX-25 | 17 | 853 |
| 13U-ATX-25 | 22 | 1459 |
| 123U-ATX-25 | 27 | 1558 |

Example 11

This example relates to UNA oligomers that can reduce V30M TTR deposits in vivo, and therefore are suitable for methods for treating or preventing conditions or diseases such as transthyretin-related amyloidosis. Transgenic mice for human TTR V30M overexpression are used at 6 months age. TTR wild-type and TTR knockout mice are used as controls. Animals are housed in controlled environment, and euthanized with ketamine and medetomidine.

For TTR gene silencing, the TTR UNA oligomer and controls are delivered in liposome formulations. Mice are injected in the tail vein with TTR UNA oligomer (n=6), at a concentration of 1 mg/kg. Untreated age-matched controls are treated with blank formulation. One injection is given per week for 4 weeks, and animals are sacrificed 48 h after last injection. Liver and colon are removed and collected to 10% formalin and frozen.

Liver and colon mRNA are isolated using phenol extraction (Invitrogen). Sciatic nerve from V30M mice is dissected from other tissue, and mRNA is extracted with a RNeasy Mini column (Qiagen). cDNA is synthesized with a SuperScript double-stranded cDNA Kit (Invitrogen). Extracted RNA is validated with Experion RNA StdSens Analysis Kit (Bio-Rad). qPCR is performed with primers and iQ Syber Green Super Mix (Bio-Rad). Double immunofluorescence analysis is performed with sciatic nerve, dorsal root ganglia, and colon from V30M animals that is removed and treated as above. Comparisons are performed with Student T-test or One-way ANOVA. Data are expressed as mean values±standard error (SEM). p-values less than 0.05 are considered significant.

Injection of any one of UNA oligomers ATX13, ATX15, ATX21, 1U-ATX25, 12U-ATX25, 13U-ATX25, 123U-ATX25, ATX37, ATX38, or ATX39, or any combination of these UNA oligomers, in V30M mice reduces the V30M TTR deposits in sciatic nerve, dorsal root ganglia, and colon by at least 90% over controls.

All publications, patents and literature specifically mentioned herein are incorporated by reference for all purposes.

It is understood that this invention is not limited to the particular methodology, protocols, materials, and reagents described, as these may vary. It is also to be understood that the terminology used herein is for the purpose of describing particular embodiments only, and is not intended to limit the scope of the present invention, which will be encompassed by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprises," "comprising", "containing," "including", and "having" can be used interchangeably.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever.

All of the features disclosed in this specification may be combined in any combination. Each feature disclosed in this specification may be replaced by an alternative feature serving the same, equivalent, or similar purpose.

What is claimed is:

1. A UNA oligomer for inhibiting expression of a target gene, the oligomer comprising a first strand and a second strand, each of the strands being 19-29 monomers in length, the monomers comprising UNA monomers and nucleic acid monomers, wherein the oligomer has a duplex structure of from 14 to 29 monomers in length, and wherein the oligomer has reduced off-target effects as compared to a siRNA with the same target, and wherein the oligomer comprises a sequence selected from the group consisting of:

| SEQ ID NO: | OLIGOMER |
|---|---|
| 49 | 5'-ĞUAACCAAGAGUAUUCCAUdTdT-3' |
| 59 | 3'-dTdTCAUUGGUUCUCAUAAGGUA-5' |
| 50 | 5'-G̃UAACCAAGAGUAUUCCAUdTdT-3' |
| 60 | 3'-ŪŪCAUUGGUUCUCAUAAGGUA-5' |
| 52 | 5'-ǦUAACCAAGAGUAUUCCAŪmU-3' |
| 62 | 3'-mUŪCAUUGGUUCUCAUAAGGUA-5' |
| 37 | 1-ÃUGUAACCAAGAGUAUUCCŪmU-3' |
| 38 | 3'-mUŪUACAUUGGUUCUCAUAAGG-5' |
| 39 | 1-ÃUGUAACCAAGAGUAUUCCŪmU-3' |
| 40 | 3'-mUŪUACAUUGGUUCUCAUAAGG-5' |
| 41 | 1-ÃUGŬAACCAAGAGUAUUCCŪmU-3' |
| 42 | 3'-mUŪUACAUUGGUUCUCAUAAGG-5' |

-continued

| SEQ ID NO: | OLIGOMER |
|---|---|
| 43 | 1-ÃUǦUAACCAAGAGUAUUCCŪmU-3' |
| 44 | 3'-mUŪUACAUUGGUUCUCAUAAGG-5' | wherein Ã represents UNA-A, Ū represents UNA-U, Ǧ represents UNA-G, mU represents a 2'-O-methyl modified U ribonucleotide, and dT represents a 2'-deoxy T nucleotide.

2. The UNA oligomer of claim 1, wherein the second strand is a guide strand for RNA interference, and the first strand is a passenger strand for RNA interference.

3. The UNA oligomer of claim 1, wherein the first and second strands are connected and form a duplex region with a loop at one end.

4. The UNA oligomer of claim 1, wherein the UNA oligomer inhibits TTR expression with reduced off-target effects.

5. The UNA oligomer of claim 1, wherein the oligomer inhibits TTR expression in vivo.

6. A pharmaceutical composition comprising a UNA oligomer of claim 1 and a pharmaceutically acceptable carrier.

7. The pharmaceutical composition of claim 6, comprising a lipid formulation.

8. The pharmaceutical composition of claim 6, comprising one or more lipids selected from cationic lipids, anionic lipids, sterols, pegylated lipids, and any combination of the foregoing.

9. The pharmaceutical composition of claim 6, wherein the composition contains liposomes.

10. A method for treating TTR-related amyloidosis, comprising administering to a subject in need an effective amount of a UNA oligomer of claim 1.

* * * * *

UNITED STATES PATENT AND TRADEMARK OFFICE
CERTIFICATE OF CORRECTION

PATENT NO. : 10,683,500 B2
APPLICATION NO. : 16/109231
DATED : June 16, 2020
INVENTOR(S) : Tachikawa et al.

Page 1 of 3

It is certified that error appears in the above-identified patent and that said Letters Patent is hereby corrected as shown below:

On the Title Page

In Item (63), under "Related U.S. Application Data", in Column 1, Line 3, delete "2015." and insert -- 2015, now abandoned. --, therefor.

In the Specification

In Column 8, Lines 1-17, delete " 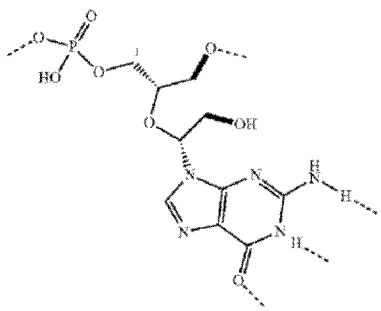 " and insert

-- 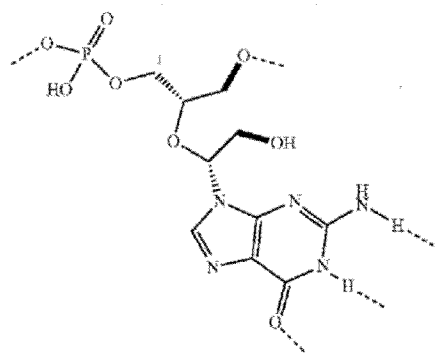 --, therefor.

In Column 10, Line 18, delete "$OR^4$, $SR^4$, $NR^4_2$," and insert -- $-OR^4$, $-SR^4$, $-NR^4_2$, --, therefor.

Signed and Sealed this
Twentieth Day of October, 2020

Andrei Iancu
*Director of the United States Patent and Trademark Office*

CERTIFICATE OF CORRECTION (continued)
U.S. Pat. No. 10,683,500 B2

In Column 10, Lines 64-65, delete "2'-0,4'-C-methylene-(D-ribofuranosyl)" and insert -- 2'-O,4'-C-methylene-(D-ribofuranosyl) --, therefor.

In Columns 13 & 14, Table 1, Under "OLIGOMER", Line 4,
delete "3-N·N·N·N·N·N·N·N·N·N·N·N·N·N·N·N·N·N·N·N-5'" and
insert -- 3'—N·N·N·N·N·N·N·N·N·N·N·N·N·N·N·N·N·N·N·N—5' --, therefor.

In Columns 13 & 14, Table 1, Under "OLIGOMER", Line 5,
delete "1-X·N·N·N·N·N·N·N·N·N·N·N·N·N·N·N·N·N·N·N-3'" and
insert -- 1—X·N·N·N·N·N·N·N·N·N·N·N·N·N·N·N·N·N·N·N—3' --, therefor.

In Columns 13 & 14, Table 1, Under "OLIGOMER", Line 7,
delete "1-X·N·N·N·N·N·N·N·N·N·N·N·N·N·N·N·N·N·X·X-3" and
insert -- 1—X·N·N·N·N·N·N·N·N·N·N·N·N·N·N·N·N·N·N·N—3' --, therefor.

In Columns 13 & 14, Table 1, Under "OLIGOMER", Line 8,
delete "3-N·N·N·N·N·N·N·N·N·N·N·N·N·N·N·N·N·N·N·N-5'" and
insert -- 3'—N·N·N·N·N·N·N·N·N·N·N·N·N·N·N·N·N·N·N·N—5' --, therefor.

In Columns 13 & 14, Table 1, Under "OLIGOMER", Line 9,
delete "1-X·N·N·N·N·N·N·N·N·N·N·N·N·N·N·N·N·N·X·X-3" and
insert -- 5'—N·N·N·N·N·N·N·N·N·N·N·N·N·N·N·N·N·N·X·X—3 --, therefor.

In Columns 13 & 14, Table 1, Under "OLIGOMER", Line 11,
delete "1-N·N·N·N·N·N·N·N·N·N·N·N·N·N·N·N·N·N·X·X-3" and
insert -- 5'—N·N·N·N·N·N·N·N·N·N·N·N·N·N·N·N·N·N·X·X—3 --, therefor.

In Columns 13 & 14, Table 1, Under "OLIGOMER", Line 12,
delete "3-N·N·N·N·N·N·N·N·N·N·N·N·N·N·N·N·N·N·N·N-5'" and
insert -- 3'—N·N·N·N·N·N·N·N·N·N·N·N·N·N·N·N·N·N·N·N—5' --, therefor.

In Columns 13 & 14, Table 1, Under "OLIGOMER", Line 13,
delete "1-N·N·N·N·N·N·N·N·N·N·N·N·N·N·N·N·N·N·N·N-3" and
insert -- 5'—N·N·N·N·N·N·N·N·N·N·N·N·N·N·N·N·N·N·N·N—3' --, therefor.

In Columns 15 & 16, Table 2, Under "OLIGOMER", Line 4,
delete "3-N·N·N·N·N·N·N·N·N·N·N·N·X·X·X·X·X·X·X·N-5'" and
insert -- 3'—N·N·N·N·N·N·N·N·N·N·N·N·X·X·X·X·X·X·X·N—5' --, therefor.

In Columns 15 & 16, Table 2, Under "OLIGOMER", Line 5,
delete "1-X·N·N·N·N·N·N·N·N·N·N·N·N·N·N·N·N·N·N·N-3" and
insert -- 1—X·N·N·N·N·N·N·N·N·N·N·N·N·N·N·N·N·N·N·N—3' --, therefor.

In Columns 15 & 16, Table 2, Under "OLIGOMER", Line 7,
delete "1-X·N·N·N·N·N·N·N·N·N·N·N·N·N·N·N·N·N·N·N-3'" and
insert -- 5'—X N N N N N N N N N N N N N N N N N N N N—3' --, therefor.

In Columns 15 & 16, Table 2, Under "OLIGOMER", Line 8,
delete "3-N·N·N·N·N·N·N·N·N·N·N·N·N·X·X·X·X·X·X·X·N-5'" and
insert -- 3'—N·N·N N N N N N N N N N N X X X X X X X N—5' --, therefor.

In Columns 15 & 16, Table 2, Under "OLIGOMER", Line 9,
delete "1-N·N·N·N·N·N·N·N·N·N·N·N·N·N·N·N·N·N·N·X·X-3'" and
insert -- 5'—N·N·N N N N N N N N N N N N N N N N N·X·X—3' --, therefor.

In Columns 15 & 16, Table 2, Under "OLIGOMER", Line 10,
delete "3-N·N·N·N·N·N·N·N·N·N·N·N·N·X·X·X·X·X·X·X·N-5'" and
insert -- 3'—N·N N N N N N N N N N N N X X X X X X X N—5' --, therefor.

In Columns 15 & 16, Table 2, Under "OLIGOMER", Line 11,
delete "1-N·N·N·N·N·N·N·N·N·N·N·N·N·N·N·N·N·N·N·X·X-3'" and
insert -- 5'—N·N N N N N N N N N N N N N N N N N N·X·X—3' --, therefor.

In Columns 15 & 16, Table 2, Under "OLIGOMER", Line 13,
delete "1-N·N·N·N·N·N·N·N·N·N·N·N·N·N·N·N·N·N·N·N-3'" and
insert -- 5'—N·N·N N N N N N N N N N N N N N N N N·N—3' --, therefor.

In Columns 15 & 16, Table 2, Under "OLIGOMER", Line 15,
delete "1-N·N·N·N·N·N·N·N·N·N·N·N·N·N·N·N·N·N·N·N-3'" and
insert -- 5'—N·N·N·N·N N N N N N N N N N N N N N·N·N—3' --, therefor.

In Columns 15 & 16, Table 2, Under "OLIGOMER", Line 16,
delete "3-N·N·N·N·N·N·N·N·N·N·N·N·N·X·X·X·X·X·X·X·N-5'" and
insert -- 3'—N·N·N·N·N·N N N N N N N X X X X X X X N—5' --, therefor.

In Column 21, Lines 7-8, delete "iQ Syber Green Super Mix (Bio-Rad)." and
insert -- iQ Sybr Green Supermix (Bio-Rad). --, therefor.

SEQUENCE LISTING

```
<160> NUMBER OF SEQ ID NOS: 83

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 1
nnnnnnnnnn nnnnnnnnnn nn                                              22

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(19)
<223> OTHER INFORMATION: a, c, u, g, unknown or other
<220> FEATURE:
```

```
<221> NAME/KEY: modified_base
<222> LOCATION: (20)..(21)
<223> OTHER INFORMATION: UNA monomer

<400> SEQUENCE: 2
nnnnnnnnnn nnnnnnnnnn n                                              21

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 3
nnnnnnnnnn nnnnnnnnnn nn                                             22

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 4
nnnnnnnnnn nnnnnnnnnn n                                              21

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 5
nnnnnnnnnn nnnnnnnnnn nn                                             22
```

```
<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, u, g, unknown or other

<400> SEQUENCE: 6
nnnnnnnnnn nnnnnnnnnn n                                              21

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(22)
<223> OTHER INFORMATION: a, c, u, g, unknown or other

<400> SEQUENCE: 7
nnnnnnnnnn nnnnnnnnnn nn                                             22

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 8
nnnnnnnnnn nnnnnnnnnn n                                              21

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(22)
<223> OTHER INFORMATION: a, c, u, g, unknown or other

<400> SEQUENCE: 9
nnnnnnnnnn nnnnnnnnnn nn                                             22
```

```
<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, u, g, unknown or other

<400> SEQUENCE: 10
nnnnnnnnnn nnnnnnnnnn n                                            21

<210> SEQ ID NO 11
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 11
nnnnnnnnnn nnnnnnnnnn nn                                           22

<210> SEQ ID NO 12
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 12
nnnnnnnnnn nnnnnnnnnn n                                            21

<210> SEQ ID NO 13
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 13
```
nnnnnnnnnn nnnnnnnnn nn                                              22

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: a, c, u, g, unknown or other

<400> SEQUENCE: 14
nnnnnnnnnn nnnnnnnnn n                                               21

<210> SEQ ID NO 15
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, u, g, unknown or other

<400> SEQUENCE: 15
nnnnnnnnnn nnnnnnnnn nn                                              22

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 16
nnnnnnnnnn nnnnnnnnn n                                               21

<210> SEQ ID NO 17
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 17
nnnnnnnnnn nnnnnnnnnn nn                                                22

<210> SEQ ID NO 18
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 18
nnnnnnnnnn nnnnnnnnnn n                                                 21

<210> SEQ ID NO 19
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 19
nnnnnnnnnn nnnnnnnnnn nn                                                22

<210> SEQ ID NO 20
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(21)
<223> OTHER INFORMATION: a, c, u, g, unknown or other

<400> SEQUENCE: 20

-continued nnnnnnnnnn nnnnnnnnnn n                                             21

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(22)
<223> OTHER INFORMATION: a, c, u, g, unknown or other

<400> SEQUENCE: 21
nnnnnnnnnn nnnnnnnnnn nn                                            22

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 22
nnnnnnnnnn nnnnnnnnnn n                                             21

<210> SEQ ID NO 23
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(22)
<223> OTHER INFORMATION: a, c, u, g, unknown or other

<400> SEQUENCE: 23
nnnnnnnnnn nnnnnnnnnn nn                                            22

<210> SEQ ID NO 24
<211> LENGTH: 21
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(21)
<223> OTHER INFORMATION: a, c, u, g, unknown or other

<400> SEQUENCE: 24
nnnnnnnnnn nnnnnnnnnn n                                                  21

<210> SEQ ID NO 25
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
<221> NAME/KEY: modified_base
<222> LOCATION: (21)..(22)
<223> OTHER INFORMATION: UNA monomer

<400> SEQUENCE: 25
nnnnnnnnnn nnnnnnnnnn nn                                                 22

<210> SEQ ID NO 26
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(21)
<223> OTHER INFORMATION: a, c, u, g, unknown or other

<400> SEQUENCE: 26
nnnnnnnnnn nnnnnnnnnn n                                                  21

<210> SEQ ID NO 27
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(20)
<223> OTHER INFORMATION: a, c, u, g, unknown or other
<220> FEATURE:
```

```
<221> NAME/KEY: modified_base
<222> LOCATION: (21)..(22)
<223> OTHER INFORMATION: UNA monomer

<400> SEQUENCE: 27
nnnnnnnnnn nnnnnnnnnn nn                                              22

<210> SEQ ID NO 28
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer

<400> SEQUENCE: 28
nnnnnnnnnn nnnnnnnnnn n                                               21

<210> SEQ ID NO 29
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, u, g, unknown or other

<400> SEQUENCE: 29
nnnnnnnnnn nnnnnnnnnn nn                                              22

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(19)
<223> OTHER INFORMATION: a, c, u, g, unknown or other
<220> FEATURE:
<221> NAME/KEY: modified_base
<222> LOCATION: (20)..(21)
<223> OTHER INFORMATION: UNA monomer
```

```
<400> SEQUENCE: 30
nnnnnnnnnn nnnnnnnnnn n                                              21

<210> SEQ ID NO 31
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(22)
<223> OTHER INFORMATION: a, c, u, g, unknown or other

<400> SEQUENCE: 31
nnnnnnnnnn nnnnnnnnnn nn                                             22

<210> SEQ ID NO 32
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: a, c, u, g, unknown or other
<220> FEATURE:
<221> NAME/KEY: modified_base
<222> LOCATION: (2)..(8)
<223> OTHER INFORMATION: UNA monomer
<220> FEATURE:
<221> NAME/KEY: modified_base
<222> LOCATION: (9)..(21)
<223> OTHER INFORMATION: a, c, u, g, unknown or other

<400> SEQUENCE: 32
nnnnnnnnnn nnnnnnnnnn n                                              21

<210> SEQ ID NO 33
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 33
aaaagggaca guauucucau u                                              21

<210> SEQ ID NO 34
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Non-nucleotide monomer
```

-continued

<400> SEQUENCE: 34
ugagaauacu gucccuuuuu u                                                    21

<210> SEQ ID NO 35
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 35
caauaaagcu ggacaagaau u                                                    21

<210> SEQ ID NO 36
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Non-nucleotide monomer

<400> SEQUENCE: 36
uucuugucca gcuuuauugu u                                                    21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 37
auguaaccaa gaguauuccu u                                                    21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Non-nucleotide monomer

<400> SEQUENCE: 38
ggaauacucu ugguuacauu u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 39
auguaaccaa gaguauuccu u                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Non-nucleotide monomer

<400> SEQUENCE: 40
ggaauacucu ugguuacauu u                                              21

<210> SEQ ID NO 41
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Non-nucleotide monomer
<220> FEATURE:
<221> NAME/KEY: modified_base
<222> LOCATION: (3)..(3)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 41
auguaaccaa gaguauuccu u                                              21

<210> SEQ ID NO 42
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Non-nucleotide monomer

<400> SEQUENCE: 42

```
ggaauacucu ugguuacauu u                                              21

<210> SEQ ID NO 43
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 43
auguaaccaa gaguauuccu u                                              21

<210> SEQ ID NO 44
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (20)..(20)
<223> OTHER INFORMATION: Non-nucleotide monomer

<400> SEQUENCE: 44
ggaauacucu ugguuacauu u                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-24 sense oligonucleotide
<220> FEATURE:
<223> OTHER INFORMATION: Description of Combined DNA/RNA Molecule:
      Synthetic ATS-24 sense oligonucleotide

<400> SEQUENCE: 45
guaaccaaga guauuccaut t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-91 sense oligonucleotide
<220> FEATURE:
<223> OTHER INFORMATION: Description of Combined DNA/RNA Molecule:
      Synthetic ATS-91 sense oligonucleotide

<400> SEQUENCE: 46
guaaccaaga guauuccaut t                                              21

<210> SEQ ID NO 47
<211> LENGTH: 21
<212> TYPE: DNA
<213> ORGANISM: Artificial Sequence
<220> FEATURE:
```

```
<223> OTHER INFORMATION: Description of Artificial Sequence: Synthetic
      ATX-14 sense oligonucleotide
<220> FEATURE:
<223> OTHER INFORMATION: Description of Combined DNA/RNA Molecule:
      Synthetic ATX-14 sense oligonucleotide

<400> SEQUENCE: 47
guaaccaaga guauuccaut t                                              21

<210> SEQ ID NO 48
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-16 sense oligonucleotide
<220> FEATURE:
<221> NAME/KEY: modified_base
<222> LOCATION: (20)..(21)
<223> OTHER INFORMATION: Non-nucleotide monomer

<400> SEQUENCE: 48
guaaccaaga guauuccauu u                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      ATX-13 sense oligonucleotide
<220> FEATURE:
<223> OTHER INFORMATION: Description of Combined DNA/RNA Molecule:
      Synthetic ATX-13 sense oligonucleotide
<220> FEATURE:
<221> NAME/KEY: modified_base
<222> LOCATION: (1)..(1)
<223> OTHER INFORMATION: Non-nucleotide monomer

<400> SEQUENCE: 49
guaaccaaga guauuccaut t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      ATX-15 sense oligonucleotide
<220> FEATURE:
<223> OTHER INFORMATION: Description of Combined DNA/RNA Molecule:
      Synthetic ATX-15 sense oligonucleotide
<220> FEATURE:
<221> NAME/KEY: modified_base
<222> LOCATION: (1)..(1)
<223> OTHER INFORMATION: Non-nucleotide monomer

<400> SEQUENCE: 50
guaaccaaga guauuccaut t                                              21

<210> SEQ ID NO 51
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-17 sense oligonucleotide
<220> FEATURE:
<221> NAME/KEY: modified_base
<222> LOCATION: (1)..(1)
<223> OTHER INFORMATION: Non-nucleotide monomer
```

```
<220> FEATURE:
<221> NAME/KEY: modified_base
<222> LOCATION: (20)..(21)
<223> OTHER INFORMATION: Non-nucleotide monomer

<400> SEQUENCE: 51
guaaccaaga guauuccauu u                                                    21

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      ATX-21 sense oligonucleotide
<220> FEATURE:
<221> NAME/KEY: modified_base
<222> LOCATION: (1)..(1)
<223> OTHER INFORMATION: Non-nucleotide monomer
<220> FEATURE:
<221> NAME/KEY: modified_base
<222> LOCATION: (19)..(19)
<223> OTHER INFORMATION: Non-nucleotide monomer

<400> SEQUENCE: 52
guaaccaaga guauuccauu                                                      20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-92 sense oligonucleotide
<220> FEATURE:
<223> OTHER INFORMATION: Description of Combined DNA/RNA Molecule:
      Synthetic ATS-92 sense oligonucleotide

<400> SEQUENCE: 53
auguaaccaa gaguauucct t                                                    21

<210> SEQ ID NO 54
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-25 sense oligonucleotide
<220> FEATURE:
<221> NAME/KEY: modified_base
<222> LOCATION: (1)..(1)
<223> OTHER INFORMATION: Non-nucleotide monomer
<220> FEATURE:
<221> NAME/KEY: modified_base
<222> LOCATION: (20)..(20)
<223> OTHER INFORMATION: Non-nucleotide monomer

<400> SEQUENCE: 54
auguaaccaa gaguauuccu u                                                    21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-24 antisense oligonucleotide
<220> FEATURE:
<223> OTHER INFORMATION: Description of Combined DNA/RNA Molecule:
      Synthetic ATS-24 antisense oligonucleotide
```

```
<400> SEQUENCE: 55
auggaauacu cuugguuact t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-91 antisense oligonucleotide
<220> FEATURE:
<223> OTHER INFORMATION: Description of Combined DNA/RNA Molecule:
      Synthetic ATS-91 antisense oligonucleotide

<400> SEQUENCE: 56
auggaauacu cuugguuact t                                              21

<210> SEQ ID NO 57
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-14 antisense oligonucleotide
<220> FEATURE:
<221> NAME/KEY: modified_base
<222> LOCATION: (20)..(21)
<223> OTHER INFORMATION: Non-nucleotide monomer

<400> SEQUENCE: 57
auggaauacu cuugguuacu u                                              21

<210> SEQ ID NO 58
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-16 antisense oligonucleotide
<220> FEATURE:
<221> NAME/KEY: modified_base
<222> LOCATION: (20)..(21)
<223> OTHER INFORMATION: Non-nucleotide monomer

<400> SEQUENCE: 58
auggaauacu cuugguuacu u                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      ATX-13 antisense oligonucleotide
<220> FEATURE:
<223> OTHER INFORMATION: Description of Combined DNA/RNA Molecule:
      Synthetic ATX-13 antisense oligonucleotide

<400> SEQUENCE: 59
auggaauacu cuugguuact t                                              21

<210> SEQ ID NO 60
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-15 antisense oligonucleotide
<220> FEATURE:
```

```
<221> NAME/KEY: modified_base
<222> LOCATION: (20)..(21)
<223> OTHER INFORMATION: Non-nucleotide monomer

<400> SEQUENCE: 60
auggaauacu cuugguuacu u                                              21

<210> SEQ ID NO 61
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-17 antisense oligonucleotide
<220> FEATURE:
<221> NAME/KEY: modified_base
<222> LOCATION: (20)..(21)
<223> OTHER INFORMATION: Non-nucleotide monomer

<400> SEQUENCE: 61
auggaauacu cuugguuacu u                                              21

<210> SEQ ID NO 62
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-21 antisense oligonucleotide
<220> FEATURE:
<221> NAME/KEY: modified_base
<222> LOCATION: (20)..(20)
<223> OTHER INFORMATION: Non-nucleotide monomer

<400> SEQUENCE: 62
auggaauacu cuugguuacu u                                              21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-92 antisense oligonucleotide
<220> FEATURE:
<223> OTHER INFORMATION: Description of Combined DNA/RNA Molecule:
      Synthetic ATS-92 antisense oligonucleotide

<400> SEQUENCE: 63
ggaauacucu ugguuacaut t                                              21

<210> SEQ ID NO 64
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-25 antisense oligonucleotide
<220> FEATURE:
<221> NAME/KEY: modified_base
<222> LOCATION: (20)..(20)
<223> OTHER INFORMATION: Non-nucleotide monomer

<400> SEQUENCE: 64
ggaauacucu ugguuacauu u                                              21

<210> SEQ ID NO 65
<211> LENGTH: 19
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 65
gtaaccaaga gtattccat                                                    19

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
tattccatat tccatattcc a                                                 21

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
atggaatact cttggttac                                                    19

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
ttggttattg gttattggtt a                                                 21

<210> SEQ ID NO 69
<211> LENGTH: 27
<212> TYPE: RNA
<213> ORGANISM: Artificial Sequence
<220> FEATURE:
<223> OTHER INFORMATION: Description of Artificial Sequence: Synthetic
      target oligonucleotide

<400> SEQUENCE: 69
cauguaacca agaguauucc auuuua                                            27

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-92 sense oligonucleotide
<220> FEATURE:
<223> OTHER INFORMATION: Description of Combined DNA/RNA Molecule:
      Synthetic ATS-92 sense oligonucleotide

<400> SEQUENCE: 70
auguaaccaa gaguauucct t                                                 21

<210> SEQ ID NO 71

<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-25 sense oligonucleotide

<400> SEQUENCE: 71
auguaaccaa gaguauuccu u                                            21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-104 oligonucleotide
<220> FEATURE:
<223> OTHER INFORMATION: Description of Combined DNA/RNA Molecule:
      Synthetic ATS-104 oligonucleotide

<400> SEQUENCE: 72
uguaaccaag aguauuccat t                                            21

<210> SEQ ID NO 73
<211> LENGTH: 21
<212> TYPE: RNA
<213> ORGANISM: Artificial Sequence
<220> FEATURE:
<223> OTHER INFORMATION: Description of Artificial Sequence: Synthetic
      ATS-37 oligonucleotide

<400> SEQUENCE: 73
uguaaccaag aguauuccau u                                            21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-91 sense oligonucleotide
<220> FEATURE:
<223> OTHER INFORMATION: Description of Combined DNA/RNA Molecule:
      Synthetic ATS-91 sense oligonucleotide

<400> SEQUENCE: 74
guaaccaaga guauuccaut t                                            21

<210> SEQ ID NO 75
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-21 sense oligonucleotide

<400> SEQUENCE: 75
guaaccaaga guauuccauu u                                            21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-105 oligonucleotide
<220> FEATURE:
<223> OTHER INFORMATION: Description of Combined DNA/RNA Molecule:

Synthetic ATS-105 oligonucleotide

<400> SEQUENCE: 76
uaaccaagag uauuccauut t                                              21

<210> SEQ ID NO 77
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-38 oligonucleotide

<400> SEQUENCE: 77
uaaccaagag uauuccauuu u                                              21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      ATS-106 oligonucleotide
<220> FEATURE:
<223> OTHER INFORMATION: Description of Combined DNA/RNA Molecule:
      Synthetic ATS-106 oligonucleotide

<400> SEQUENCE: 78
ccaagaguau uccauuuuut t                                              21

<210> SEQ ID NO 79
<211> LENGTH: 21
<212> TYPE: RNA
<213> ORGANISM: Artificial Sequence
<220> FEATURE:
<223> OTHER INFORMATION: Description of Artificial Sequence: Synthetic
      ATX-39 oligonucleotide

<400> SEQUENCE: 79
ccaagaguau uccauuuuuu u                                              21

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (1)..(19)
<223> OTHER INFORMATION: a, c, t, g, unknown or other

<400> SEQUENCE: 80
nnnnnnnnnn nnnnnnnnnt t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<220> FEATURE:
<221> NAME/KEY: modified_base
<222> LOCATION: (1)..(19)
<223> OTHER INFORMATION: a, c, t, g, unknown or other

<400> SEQUENCE: 81
nnnnnnnnnn nnnnnnnnnt t                                              21

<210> SEQ ID NO 82
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: UNA monomer
<220> FEATURE:
<221> NAME/KEY: modified_base
<222> LOCATION: (2)..(20)
<223> OTHER INFORMATION: a, c, u, g, unknown or other
<220> FEATURE:
<221> NAME/KEY: modified_base
<222> LOCATION: (21)..(21)
<223> OTHER INFORMATION: UNA monomer

<400> SEQUENCE: 82
nnnnnnnnnn nnnnnnnnnn nu                                             22

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(19)
<223> OTHER INFORMATION: a, c, u, g, unknown or other
<220> FEATURE:
<221> NAME/KEY: modified_base
<222> LOCATION: (20)..(20)
<223> OTHER INFORMATION: UNA monomer

<400> SEQUENCE: 83
nnnnnnnnnn nnnnnnnnn u                                               21
```